US009883936B2

(12) United States Patent
Sutton et al.

(10) Patent No.: US 9,883,936 B2
(45) Date of Patent: Feb. 6, 2018

(54) ATRIAL APPENDAGE BLOOD FILTRATION SYSTEMS

(71) Applicant: ATRITECH, INC., Plymouth, MN (US)

(72) Inventors: Gregg S. Sutton, Maple Grove, MN (US); Jeffrey Welch, Maple Grove, MN (US); Dean A. Peterson, Rogers, MN (US); John B. Bridgeman, Minneapolis, MN (US); Bruce R. Youngberg, Ramsey, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 237 days.

(21) Appl. No.: 14/806,446

(22) Filed: Jul. 22, 2015

(65) Prior Publication Data
US 2016/0051358 A1    Feb. 25, 2016

Related U.S. Application Data

(63) Continuation of application No. 10/351,736, filed on Jan. 24, 2003, now abandoned.
(Continued)

(51) Int. Cl.
*A61M 29/00* (2006.01)
*A61F 2/01* (2006.01)
(Continued)

(52) U.S. Cl.
CPC ............ *A61F 2/01* (2013.01); *A61B 17/0057* (2013.01); *A61B 17/12122* (2013.01);
(Continued)

(58) Field of Classification Search
CPC .......... A61B 17/0057; A61B 17/12122; A61B 17/12172; A61B 2017/00243;
(Continued)

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| WO | 9313712 A1 | 7/1993 |
| WO | 9721402 A1 | 6/1997 |

(Continued)

OTHER PUBLICATIONS

Cragg, et al., "A New Percutaneous Vena Cava Filter," ALJ, 141: 601-604, Sep. 1983.
(Continued)

*Primary Examiner* — Robert Lynch
(74) *Attorney, Agent, or Firm* — Seager, Tufte & Wickhem LLP

(57) ABSTRACT

Instrumentation for percutaneous delivery of blood filtration devices to atrial appendages includes a curved access sheath and a delivery tube. A compressed filter device attached to a tether wire is loaded in the delivery tube. The access sheath and the delivery tube can be mechanically locked and moved together to place the device in a suitable deployment position. The device is deployed by expelling it from the delivery tube either by retracting the delivery tube over the tether wire, or by moving the tether wire forward through the delivery tube. A filter membrane in the deployed device extends across the appendage ostium to filter blood flow through the ostium. The filter membrane is configured to present a flat surface to atrial blood flow past the ostium.

20 Claims, 18 Drawing Sheets

Related U.S. Application Data

(60) Provisional application No. 60/417,110, filed on Oct. 8, 2002, provisional application No. 60/403,720, filed on Aug. 14, 2002, provisional application No. 60/379,921, filed on May 10, 2002, provisional application No. 60/351,898, filed on Jan. 25, 2002.

(51) Int. Cl.
*A61B 17/00* (2006.01)
*A61B 17/12* (2006.01)

(52) U.S. Cl.
CPC .. *A61B 17/12172* (2013.01); *A61B 17/12022* (2013.01); *A61B 2017/00243* (2013.01); *A61B 2017/00575* (2013.01); *A61B 2017/12095* (2013.01); *A61F 2002/011* (2013.01); *A61F 2002/016* (2013.01); *A61F 2002/018* (2013.01); *A61F 2230/005* (2013.01); *A61F 2230/0006* (2013.01); *A61F 2230/008* (2013.01); *A61F 2230/0093* (2013.01)

(58) Field of Classification Search
CPC  A61B 2017/00575; A61B 2017/00592; A61B 2017/00601; A61F 2/01; A61F 2/013; A61F 2002/011; A61F 2002/016
See application file for complete search history.

(56) References Cited

U.S. PATENT DOCUMENTS

| | | |
|---|---|---|
| 3,844,302 A | 10/1974 | Klein |
| 3,874,388 A | 4/1975 | King et al. |
| 4,007,743 A | 2/1977 | Blake |
| 4,341,218 A | 7/1982 | Ü |
| 4,585,000 A | 4/1986 | Hershenson |
| 4,603,693 A | 8/1986 | Conta et al. |
| 4,665,906 A | 5/1987 | Jervis |
| 4,710,192 A | 12/1987 | Liotta et al. |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 5,037,810 A | 8/1991 | Sabila, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,078,736 A | 1/1992 | Behl |
| 5,108,420 A | 4/1992 | Marks |
| 5,171,259 A | 12/1992 | Inoue |
| 5,171,383 A | 12/1992 | Sagae et al. |
| 5,176,692 A | 1/1993 | Wilk et al. |
| 5,192,301 A | 3/1993 | Kamiya et al. |
| 5,256,146 A | 10/1993 | Ensminger et al. |
| 5,258,042 A | 11/1993 | Mehta |
| 5,284,488 A | 2/1994 | Sideris |
| 5,306,234 A | 4/1994 | Johnson |
| 5,334,217 A | 8/1994 | Das |
| 5,350,399 A | 9/1994 | Erlebacher et al. |
| 5,353,784 A | 10/1994 | Nady-Mohamed |
| 5,370,657 A | 12/1994 | Irie |
| 5,375,612 A | 12/1994 | Cottenceau et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,702,421 A | 12/1997 | Schneidt |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,810,874 A | 9/1998 | Lefebvre |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,846,260 A | 12/1998 | Maahs |
| 5,846,261 A | 12/1998 | Kotula et al. |
| 5,849,005 A | 12/1998 | Garrison et al. |
| 5,851,232 A | 12/1998 | Lois |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,882,340 A | 3/1999 | Yoon |
| 5,885,258 A | 3/1999 | Sachdeva et al. |
| 5,895,399 A | 4/1999 | Barbut et al. |
| 5,902,289 A | 5/1999 | Swartz et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,931,818 A | 8/1999 | Werp et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,954,694 A | 9/1999 | Sunseri |
| 5,957,940 A | 9/1999 | Tanner et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |

(56) References Cited

U.S. PATENT DOCUMENTS

| | | | |
|---|---|---|---|
| 6,048,331 | A | 4/2000 | Tsugita et al. |
| 6,051,014 | A | 4/2000 | Jang |
| 6,051,015 | A | 4/2000 | Maahs |
| 6,056,720 | A | 5/2000 | Morse |
| 6,068,621 | A | 5/2000 | Balceta et al. |
| 6,074,357 | A | 6/2000 | Kaganov et al. |
| 6,079,414 | A | 6/2000 | Roth |
| 6,080,182 | A | 6/2000 | Shaw et al. |
| 6,080,183 | A | 6/2000 | Tsguita et al. |
| 6,083,239 | A | 7/2000 | Addis |
| 6,132,438 | A | 10/2000 | Fleischman et al. |
| 6,136,016 | A | 10/2000 | Barbut et al. |
| 6,139,527 | A | 10/2000 | Laufer et al. |
| 6,152,144 | A | 11/2000 | Lesh et al. |
| 6,161,543 | A | 12/2000 | Cox et al. |
| 6,193,739 | B1 | 2/2001 | Chevillon et al. |
| 6,203,531 | B1 | 3/2001 | Ockuly et al. |
| 6,231,561 | B1 | 5/2001 | Frazier et al. |
| 6,231,589 | B1 | 5/2001 | Wessman et al. |
| 6,328,755 | B1 | 12/2001 | Marshall |
| 6,533,782 | B2 | 3/2003 | Howell et al. |
| 6,589,214 | B2 | 7/2003 | McGuckin et al. |
| 6,641,564 | B1 | 11/2003 | Kraus |
| 6,650,923 | B1 | 11/2003 | Lesh et al. |
| 6,755,812 | B2 | 6/2004 | Peterson et al. |
| 7,044,134 | B2 | 5/2006 | Khairkhahan et al. |
| 2003/0057156 | A1 | 3/2003 | Peterson et al. |
| 2003/0220667 | A1 | 11/2003 | van der Burg et al. |

FOREIGN PATENT DOCUMENTS

| | | | |
|---|---|---|---|
| WO | 9726939 | A1 | 7/1997 |
| WO | 9728749 | A1 | 8/1997 |
| WO | 9802100 | A1 | 1/1998 |
| WO | 9817187 | A1 | 4/1998 |
| WO | 9823322 | A1 | 6/1998 |
| WO | 9907289 | A1 | 2/1999 |
| WO | 9908607 | A1 | 2/1999 |
| WO | 9930640 | A1 | 6/1999 |
| WO | 9959479 | A1 | 11/1999 |
| WO | 0001308 | A1 | 1/2000 |
| WO | 0027292 | A1 | 5/2000 |
| WO | 0053120 | A1 | 9/2000 |
| WO | 0121247 | A1 | 3/2001 |
| WO | 0126726 | A1 | 4/2001 |
| WO | 0130266 | A1 | 5/2001 |

OTHER PUBLICATIONS

Cragg et al., "Nonsurgical Placement of Arterial Endoprosthesis: A New Technique Using Nitinol Wire," Radiology vol. 147, No. 1, pp. 261-263, Apr. 1983.
Lock et al., "Transcatheter Closure of Atrial Septal Defects," Circulation, vol. 79(5), 1091-1099, May 1989.
Lock et al., "Transcatheter Umbrella Closure of Congenital Heart Defects," Circulation, vol. 75(3), 593-599, 1987.
Rashkind et al., "Nonsurgical Closure of patent ductus arteriosus: clinical application of the Rashkind PDA Occluder System," Circulation, vol. 75(3), 583-592, 1987.
Ruttenberg, "Nonsurgical Therapy of Cardiac Disorders," Pediatric Consult, vol. 5(2), 1986.
Sugita et al., "Nonsurgical Implantation of a Vascular Ring Prothesis Using Thermal Shape Memory Ti/Ni Alloy (Nitinol Wire)," Trans. Am. Soc. Artif. Intern. Organs, vol. XXXII, 30-34, 1986.
Wessel et al., "Outpatient Closure of the patent ductus arteriosus," Circulation, vol. 77(5), 1068-1071, 1988.
All Foreign and NPL References Have Been Previously Provided in Parent U.S. Appl. No. 10/351,736, filed Jan. 24, 2003.

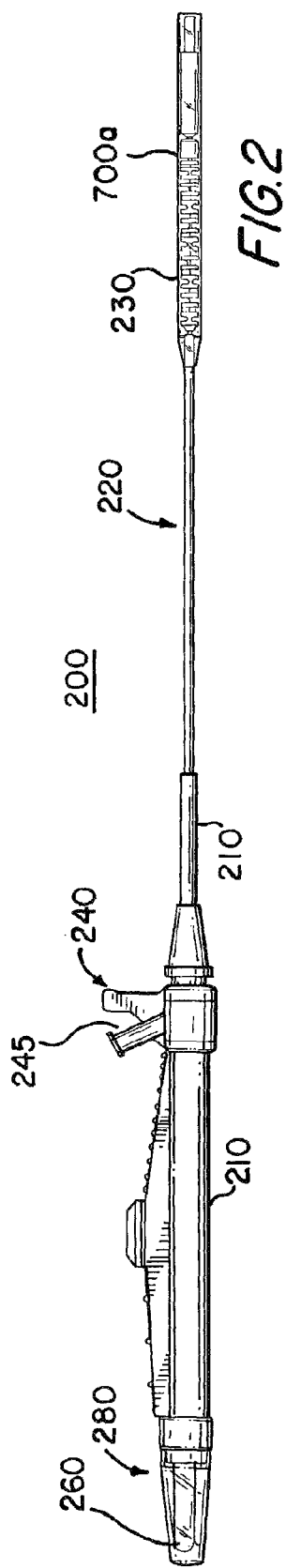
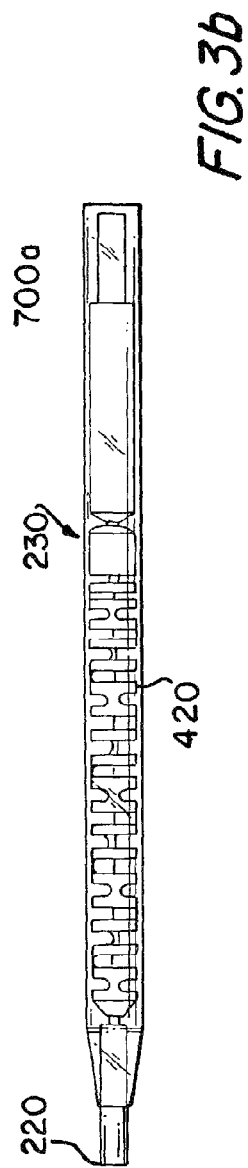
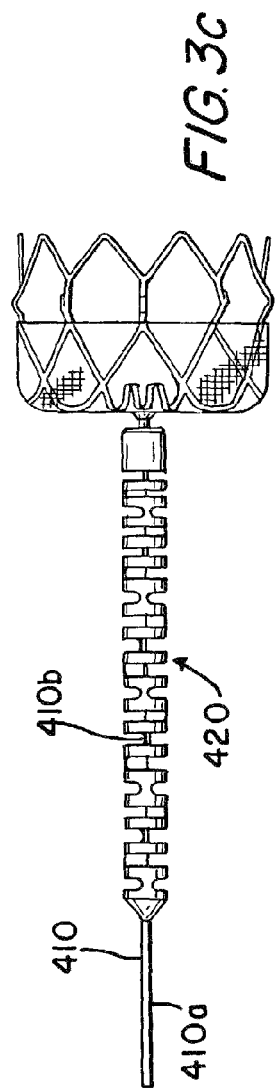

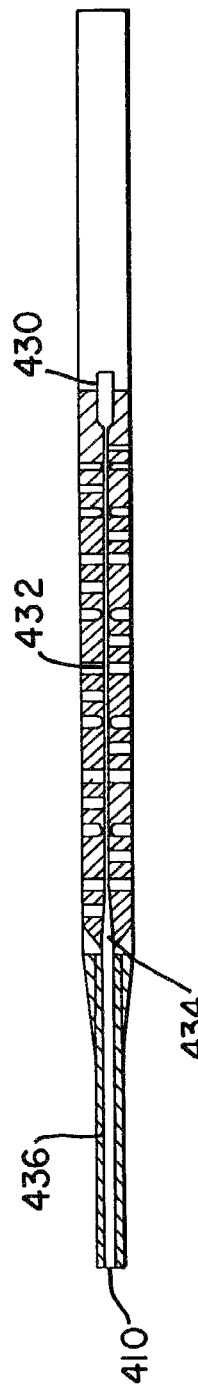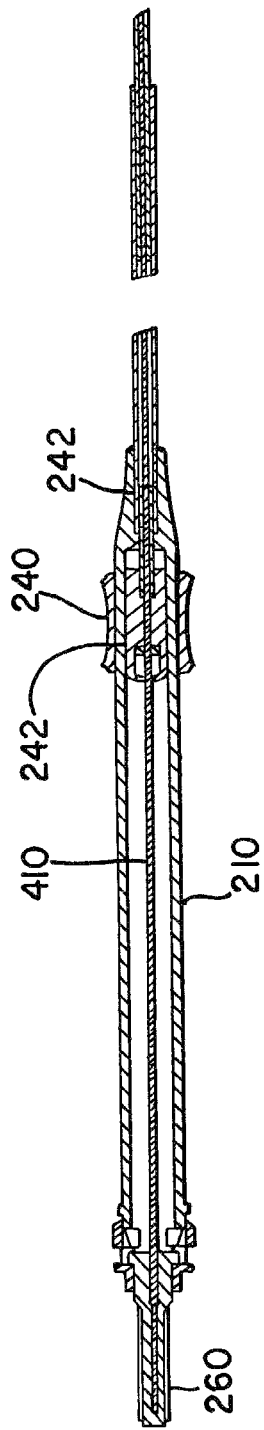

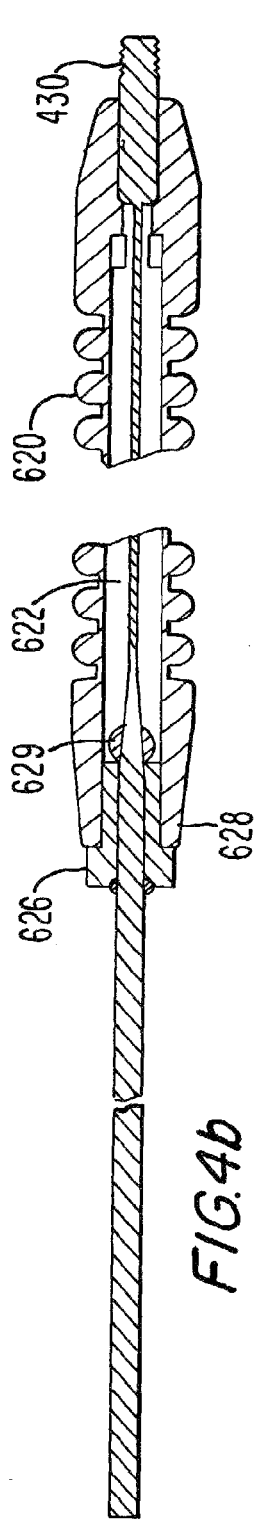
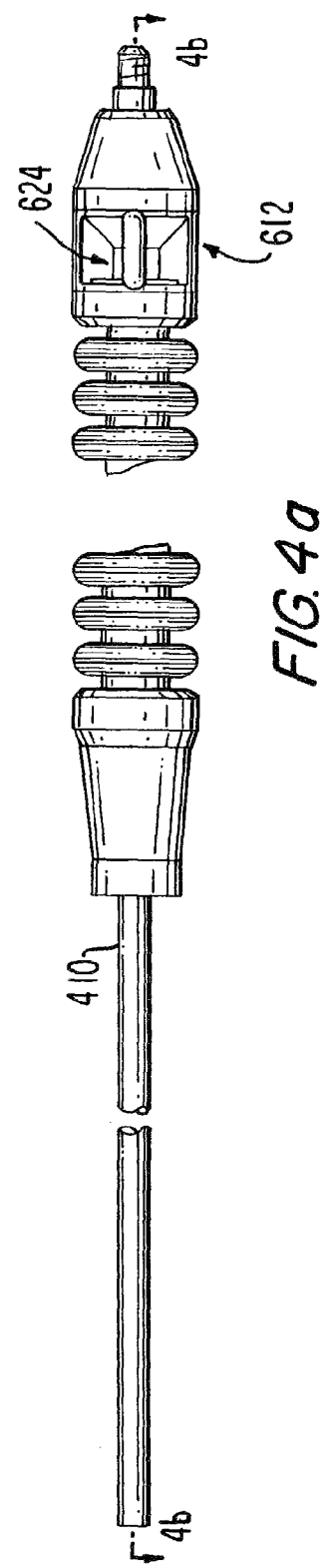
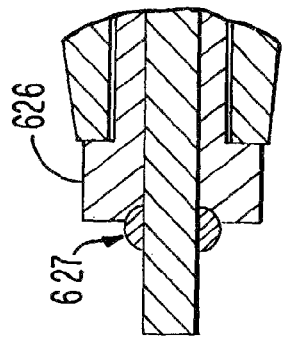
FIG.4a
FIG.4b
FIG.4c

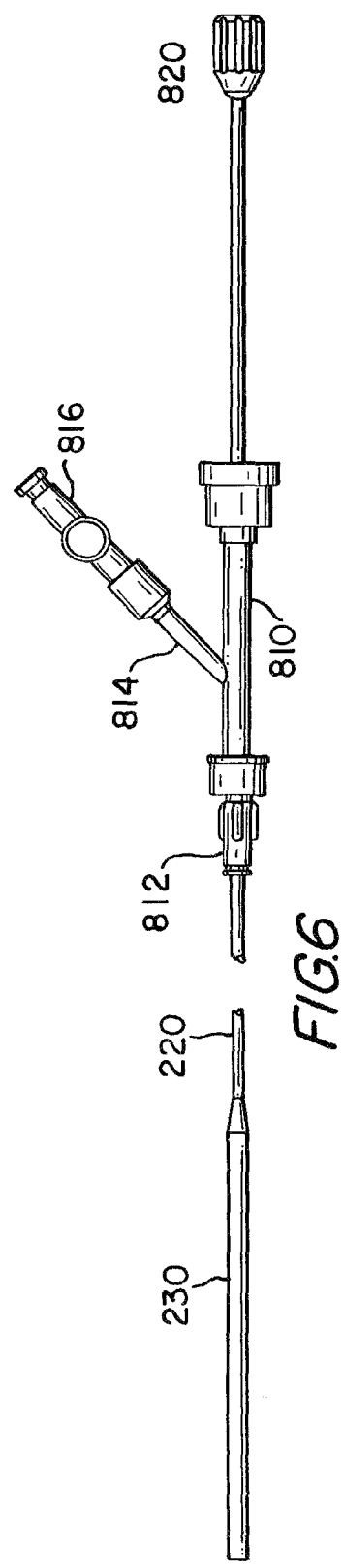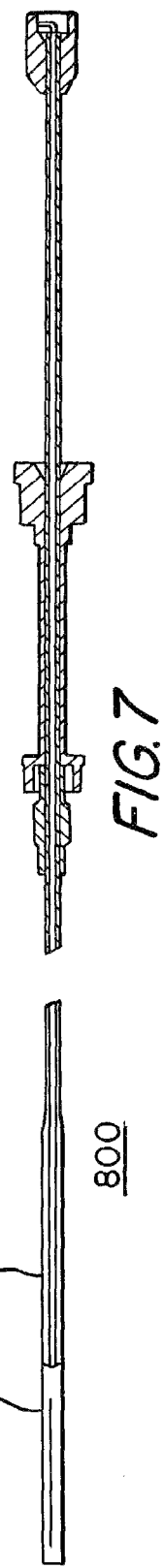

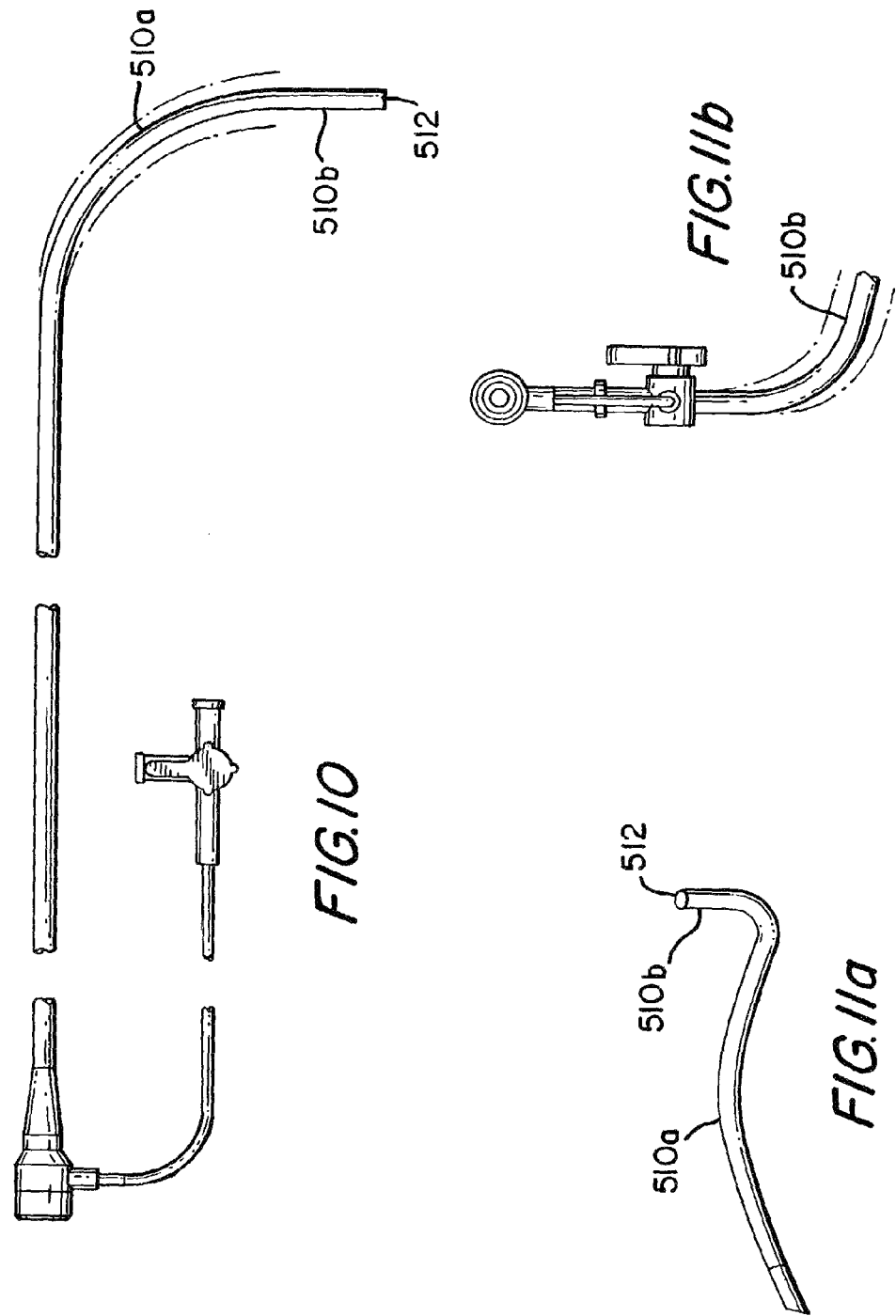

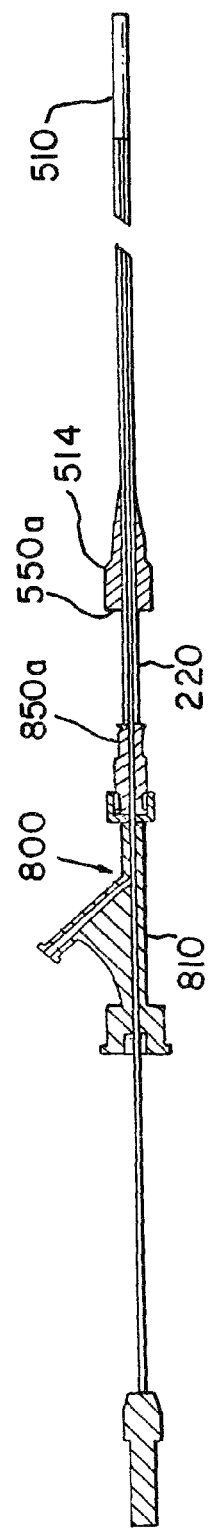

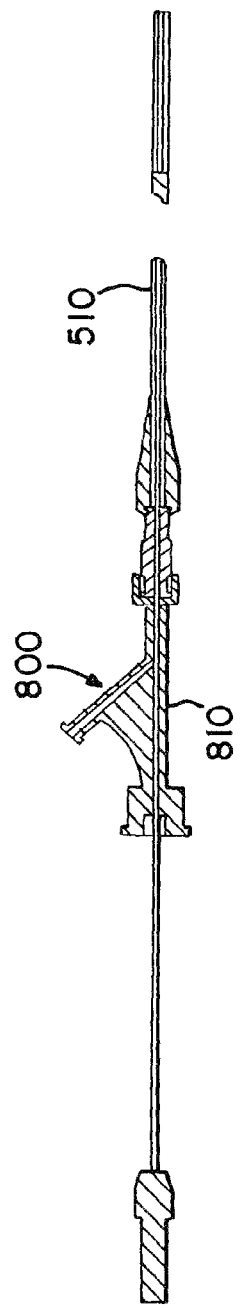

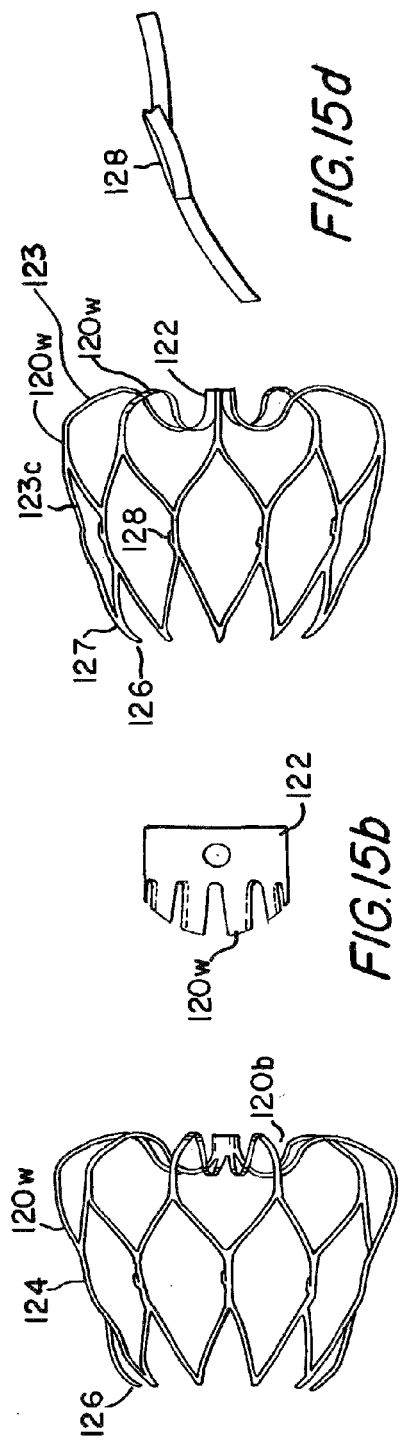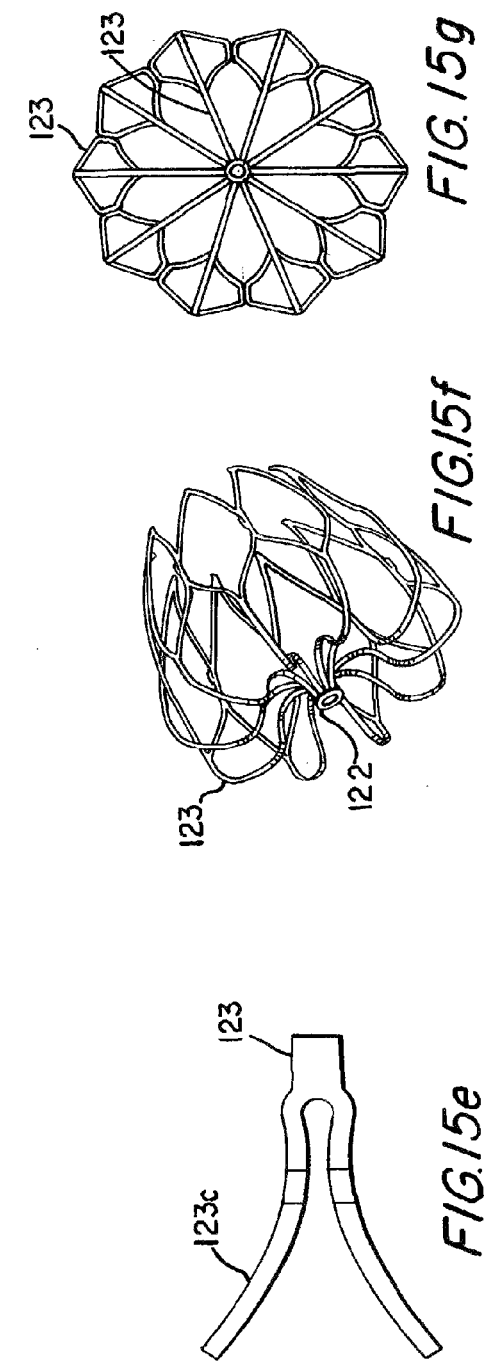

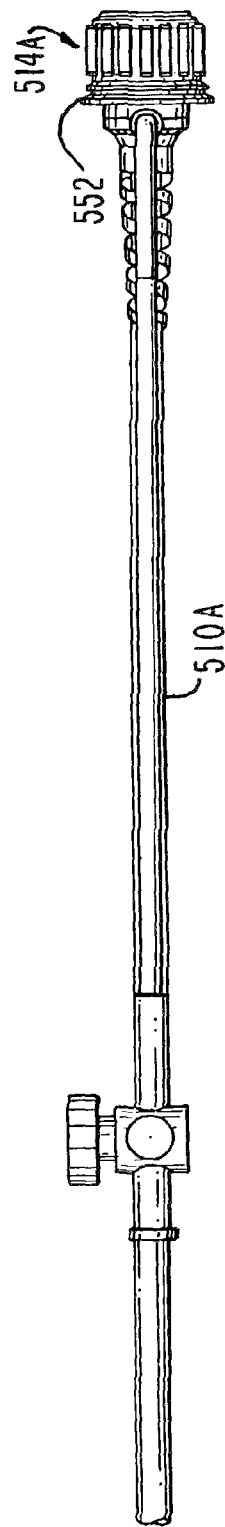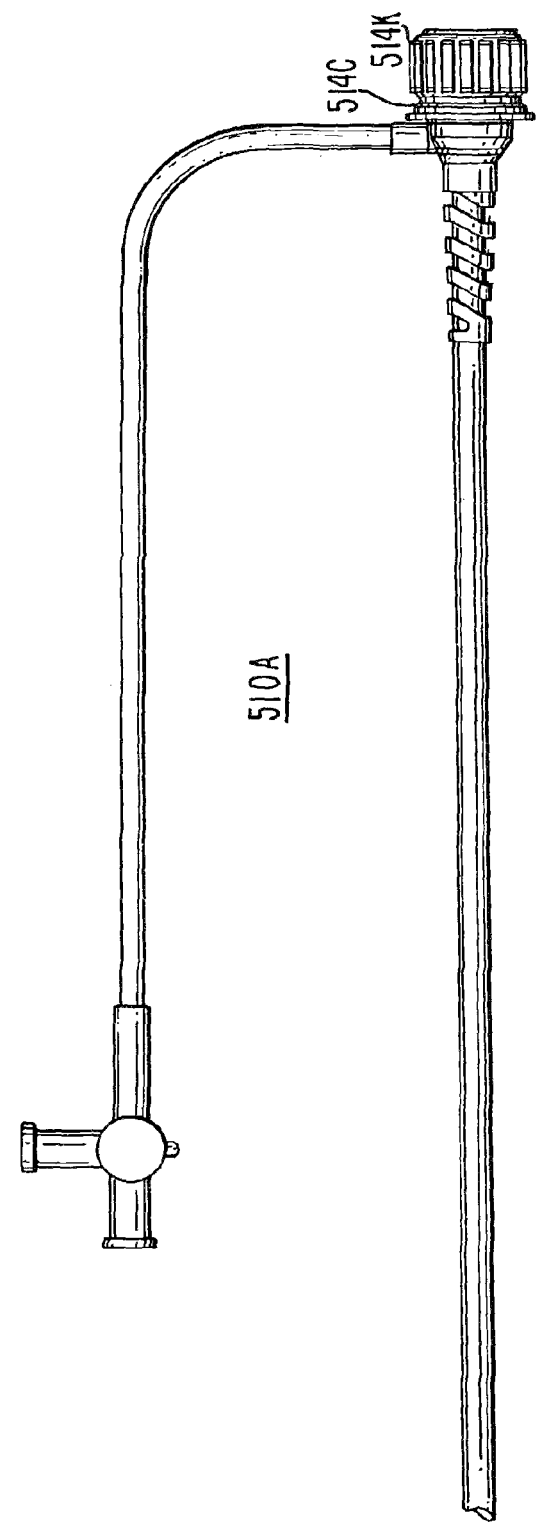

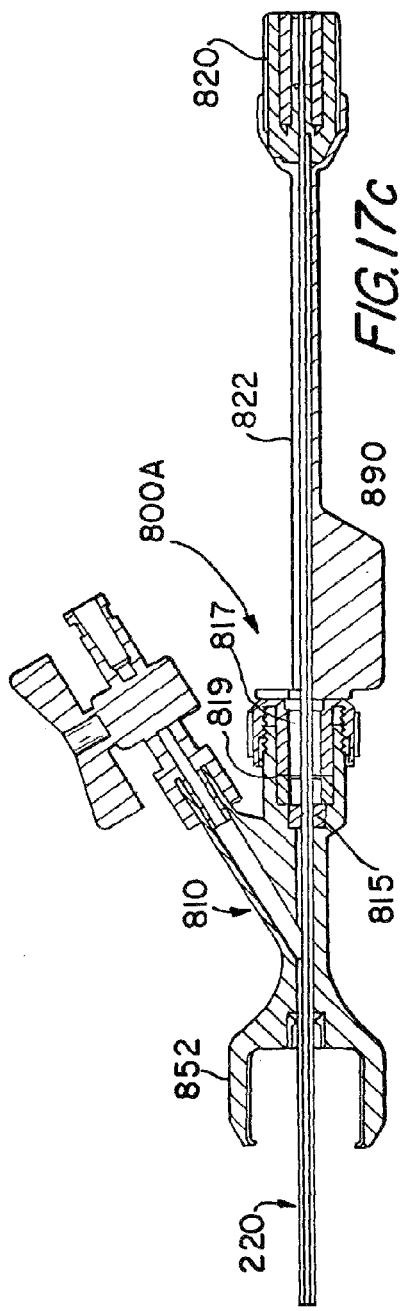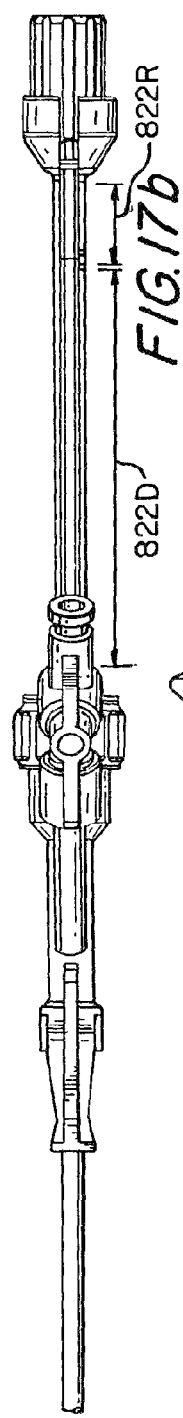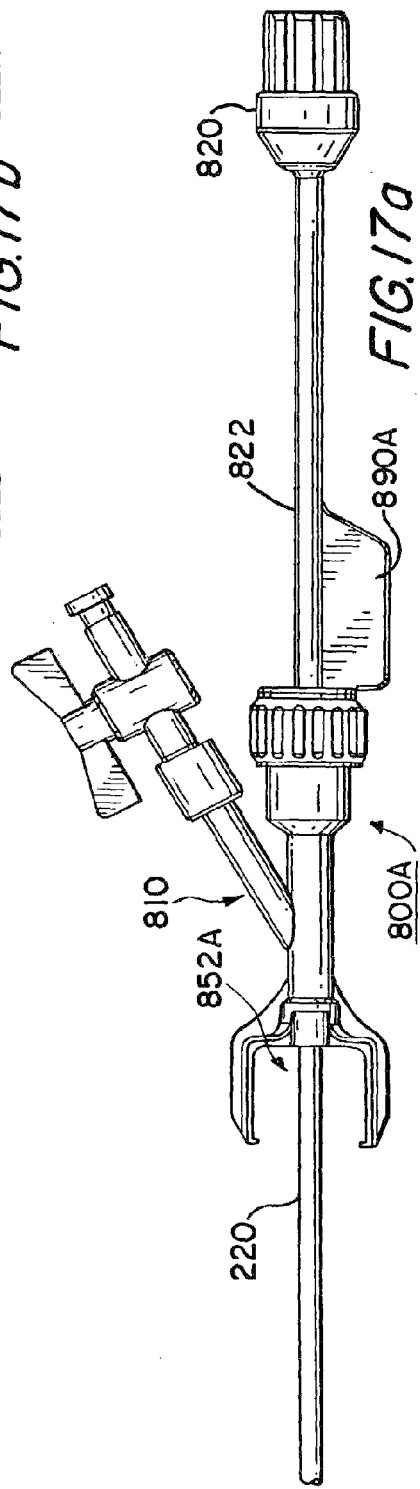

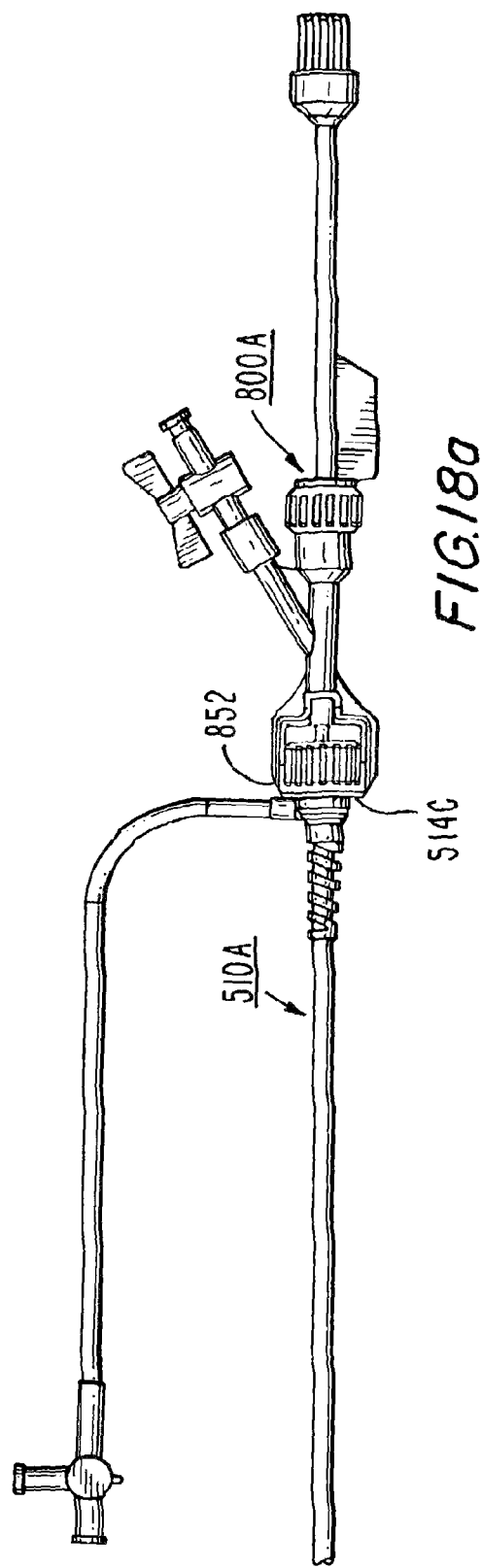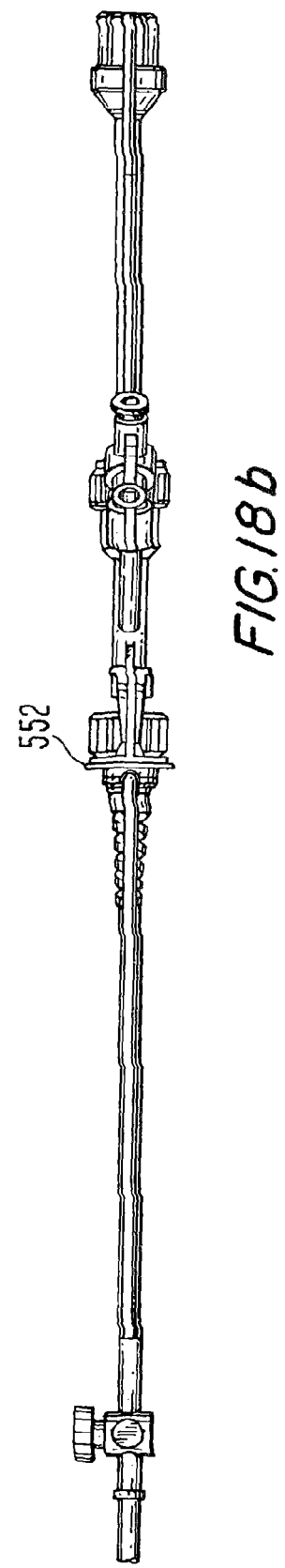

ATRIAL APPENDAGE BLOOD FILTRATION SYSTEMS

This application is a continuation of U.S. application Ser. No. 10/351,736, filed Jan. 24, 2003, now abandoned, which claims the benefit of U.S. provisional application No. 60/351,898, filed Jan. 25, 2002, U.S. provisional application No. 60/379,921, filed May 10, 2002, U.S. provisional application No. 60/417,110, filed Oct. 8, 2002, and U.S. provisional application No. 60/403,720, filed Aug. 14, 2002, all of which are hereby incorporated by reference in their entireties herein.

BACKGROUND OF THE INVENTION

The invention relates to filtration of cardiac blood flow between an atrial appendage and its associated atrium. The blood filtration prevents the dispersal of thrombi, which may be formed in the atrial appendage, into the body's blood circulation system. In particular the invention relates to implant filter devices, and apparatus for the percutaneous delivery and implantation of such devices in the heart.

Structural heart disease or other cardiac conditions in a patient can result in atrial fibrillation, which in turn causes blood to pool or stagnate in the patient's atrial appendage. Thrombi (i.e., blood clots) are prone to form in the atrial appendages with stagnant blood. The blood clots may subsequently break off and migrate to the brain leading to stroke, or to other parts of the body causing loss of circulation to the affected organ. The left atrial appendage (LAA), which is anatomically disposed on top of the left atrium, happens to be a particularly likely site for harmful blood clot formation. Thromboembolic events such as strokes are frequently traced to blood clots from the LAA.

The risk of stroke in patients with atrial fibrillation may be reduced by drug therapy, for example, by using blood thinners such as Coumadin. However, not all patients cannot tolerate or handle the blood thinning drugs effectively. Alternative methods for reducing the risk of stroke involve surgery to remove or obliterate the LAA. Other proposed methods include using mechanical devices to occlude the atrial appendage opening and thereby stop blood flow from the atrial appendage into its associated atrium.

Another prophylactic method for avoiding strokes or other thromboembolic events caused by blood clots formed in atrial appendages involves filtering harmful emboli from the blood flowing out of the atrial appendages. Co-pending and co-owned U.S. patent application Ser. No. 09/428,008, U.S. patent application Ser. No. 09/614,091, U.S. patent application Ser. No. 09/642,291, U.S. patent application Ser. No. 09/697,628, U.S. patent application Ser. No. 09/932,512, U.S. patent application Ser. No. 09/960,749, U.S. patent application Ser. No. 10/094,730, U.S. patent application Ser. No. 10/198,261, and U.S. patent application Ser. No. 10/200,565, all of which are hereby incorporated by reference in their entireties herein, describe filtering devices which may be implanted in an atrial appendage to filter the blood flowing out of the atrial appendage. The devices may be delivered percutaneously to the heart through the body's blood vessels using common cardiac catheterization methods. These catheterization procedures often involve first deploying an access system to position an access sheath through a patient's vascular system to the interior locations in the patient's heart. The access sheath provides a passageway through which implant devices are passed from outside the patient's body to interior locations in the heart. Delivery of the devices to the LAA may involve transseptal catheterization procedures, in which access to the left atrium is gained from the right atrium by puncturing the intervening septum. One or more independent delivery systems may be used to deliver the devices through the access sheath.

U.S. patent application Ser. No. 09/932,512, U.S. patent application Ser. No. 10/094,730, and U.S. patent application Ser. No. 10/200,565, disclose expandable implant devices which are small and which can be delivered percutaneously by catheters to the atrial appendages. The effectiveness or success of medical procedures using the implant devices may depend on the proper deployment and retention of the devices in a suitable orientation in the atrial appendages. U.S. patent application Ser. No. 09/960,749 discloses a catheter apparatus having position guides. U.S. patent application Ser. No. 10/198,260 discloses a catheter apparatus having a device tether, which allows a deployed device to be retrieved for repositioning as necessary.

Consideration is now being given to improving implant devices and to improving catheterization apparatus including access and delivery systems for the percutaneous delivery of such devices through geometrically complex vascular paths leading, for example, to the left atrial appendage.

SUMMARY OF THE INVENTION

The invention provides instrumentation for percutaneously implanting filter devices in atrial appendages to filter blood flowing between the atrial appendages and associated atrial chambers. The filter devices are designed to prevent dispersal of blood clots formed in the atrial appendages into the body's blood circulation system.

The filter devices are self-expanding elastic or compressible frames made from chicken wire-like mesh. The wire frames are made of shape-memory alloy materials such as nitinol. A typical device at its natural or expanded size may be about an inch in diameter and about an inch long. The wire frames may have a generally cylindrical or conical shape with a closed end. A blood-permeable filter membrane covers the closed end. The filter-membrane covered closed end extends across the ostium of a subject atrial appendage in which a device is used. In one embodiment, the filter membrane is made of a polyester weave or knit having a nominal hole size of about 125 um. The filter membrane filters harmful-sized emboli from the blood flow between the appendage and the atrium.

The wire frame sides are shaped for an interference fit in the subject atrial appendage in which the device is used. The closed end wire sections may be S-shaped and serve as resilient springs, which push or bias the cylindrical side portions of the wire frame outward. Additionally, tissue-engaging barbs are disposed on the wire frame to aid or encourage retention of the device at its implant location. The wire frames have sockets or other fixtures for attaching a delivery tether wire or shaft. The attachment sockets are disposed about longitudinal frame axis at or about the wire frames' closed ends. The wire frames are suitably recessed to accommodate the attachment sockets so that closed ends of the devices (the supported filter membranes) have a substantially undulating or flat surface topography.

The filter devices may be percutaneously implanted in a patient's atrial appendage. Inventive device delivery systems and instrumentation may be used for the implant procedures. The instrumentation includes a curved tubular access sheath. The implant procedures involve introducing the access sheath into the patient's blood vessels through a skin puncture and coursing it through a patient's vascular system to the interior locations in the patient's heart, for example, across the atrial septum. The coursed access sheath establishes a channel or passageway for device delivery to an atrial appendage through the patient's vasculature.

The distal portions of the access sheath are curved. The curvatures may be simple or compound. The curvatures take into account the anatomical geometry of the heart and are designed to provide a passageway leading directly to the subject atrial appendage. In an embodiment, the access sheath is made from J-shape tubing, with a distal portion that has a bend of about 90 degrees. In another embodiment, the access sheath is made from similar J-shape tubing, the distal portion of which has a further second bend away from the J-shape plane.

In a transseptal device implantation procedure the suitably curved access sheath may be set up across the septum so that its distal end is directed toward the subject LAA. Access sheath may be further advanced into the LAA itself if so desired.

A device delivery system may be used to move a filter device through the pre-positioned access sheath. The delivery system includes a delivery catheter tube that extends into a tubular implant sheath. The filter device that is to be implanted is attached to a tether wire or shaft passing through the delivery catheter tube. The tether wire or shaft is made from flexible wire material (e.g., nitinol). A threaded fixture at the end of the tether wire may be used for device attachment. The attached filter device is compressed to a narrow diameter size and confined in the implant sheath extending from the delivery catheter tube.

The delivery catheter tube (with the device loaded in the implant sheath) is inserted into the pre-positioned access sheath leading to the subject atrial appendage. The implant sheath is advanced through the access sheath to a suitable device deployment location. The delivery system and access sheath may include mechanical couplers or adapters to lock the delivery tube to the access sheath. When locked together, the delivery catheter tube and the access sheath may be moved together, for example, to place or orient implant sheath in the suitable device deployment location. The device is deployed by expelling it from the implant sheath at a suitable location in or about the subject atrial appendage. On expulsion from the confining implant sheath the filter device self-expands to its useful size.

The delivery system may include remote actuators to expel or uncover filter devices for deployment. In one embodiment, a knob or handle is attached to the proximal end of the tether wire. The knob may be manipulated to translate or turn the tether wire. The tether wire is translated through the delivery tube to push the confined implant device out of the implant sheath. The tether wire diameter is selected to provide sufficient rigidity for transmitting mechanical translation and rotational forces to the attached implant device. Portions of the tether wire close to the attached implant device have a reduced diameter to reduce the coupling stiffness of the tether wire to the attached implant device. This reduced coupling stiffness is advantageous in deploying the device in its natural unbiased state while it is still attached to the tether wire.

In another embodiment of the delivery system, additionally or alternatively, the delivery tube is partially retractable over the tether wire into a handle portion. A sliding actuator, which is attached to the delivery tube, is disposed on the handle portion. The filter device may be expelled from the implant sheath by retracting delivery tube into the handle portion by activating the actuator on the handle portion. In either embodiment, distal portions of the tether wire adjoining the attached device may be encased in a flexible elastomeric material coil, which occupies the implant sheath lumen around the tether wire. The flexible coil reduces any buckling tendencies, which a moving flexible tether wire may have. Next, the tether wire may be detached by unscrewing it from the deployed device by turning a knob attached to the proximal end the tether wire. The delivery system may include mechanical features or releasable stops to limit the translation or rotation of the tether wire. Use of the releasable stops limits the possibilities for inadvertent expulsion of the device from the implant sheath and inadvertent release or loosening of the device attachment.

Both the access sheath and the delivery system tubes have suitable valve assemblies attached to their proximal ends to prevent fluid leakage during the device implantation procedure. The valve assemblies may include ports for injection of fluids through the various tube lumens. For example, the delivery catheter tube may be attached to a large bore Tuohy-Borst valve assembly. The Y-arm of the valve assembly may be used for intermittent or continuous fluid flushing and contrast injection or for continuous blood monitoring during the implantation procedure.

BRIEF DESCRIPTION OF THE DRAWINGS

FIG. 2 is a side elevational view of an inventive delivery system including a delivery catheter tube having an implant sheath attached to its distal end. The implant sheath contains an unexpanded filter device attached to a distal flex coil end of a tether wire passing through the delivery tube lumen.

FIG. 3a is an enlarged cross sectional view of a distal section of the delivery system of FIG. 2 with the distal flex coil end of a tether wire extending into the implant sheath in accordance with the principles of the invention.

FIG. 3b is a side elevational view of the implant sheath of FIG. 3a containing an unexpanded filter device attached the distal flex coil end of the tether wire extending into the implant sheath in accordance with the principles of the invention.

FIG. 3c is a side elevational view an unsheathed and expanded filter device attached to the distal flex coil end of the tether wire of FIG. 3a in accordance with the principles of the invention.

FIGS. 4a and 4b respectively are a side elevational and a cross-sectional view of a flexible coil portion that encases the tether wire in accordance with the principles of the invention. The inset FIG. 4c is an enlarged view of a portion of FIG. 4b showing details of the mechanical attachment of flexible coil portion and the encased tether wire.

FIG. 5 is an enlarged cross sectional view of the proximal portion of the delivery system of FIG. 2.

FIGS. 6 and 7 respectively are a side elevational view and a plan view of another catheter delivery system in accordance with the principles of the invention. The delivery system includes a delivery tube extending into a larger diameter implant sheath and a tether wire having a control knob at its proximal end. The inset in FIG. 7 is an enlarged view of section B showing details of the mechanical attachment of flexible coil portion and the encased tether wire.

FIG. 10 is a plan view of an access system sheath in which the sheath tip has compound curvatures in accordance with the principles of the invention.

FIG. 11a is a side elevation view of the sheath tip portions of the access system sheath of FIG. 10.

FIG. 11b is a rear elevation view of the access system sheath of FIG. 10.

FIG. 12a is a cross sectional view of a delivery system tube inserted in an access system sheath in accordance with the principles of the present invention. The delivery system tube is partially inserted in the access system sheath.

FIG. 12b is a view similar to that of FIG. 12b illustrating the delivery system tube inserted in and locked with the access system sheath. In the locked position the distal tips of the two are about flush. Inset B is an enlarged view of the locking portions of the delivery tube and the access system sheath.

FIG. 13b is a partial side elevational view of the expanded wire frame structure of the filter device of FIG. 13a.

FIG. 14b is plan view of the proximal end of the device shown in FIG. 14a.

FIG. 15a is a side elevational view of the expanded wire frame structure of the device of FIG. 14a in accordance with the principles of the invention.

FIG. 15b is an enlarged view of portion A of the wire frame of FIG. 15a illustrating the detailed configuration of the wire frame collar in accordance with the principles of the invention.

FIG. 15c shows another side elevational view of the wire frame of FIG. 15a, which has been rotated by about 15 degrees around the device's cylindrical axis.

FIG. 15d is an enlarged view of a barb-carrying portion C of the wire frame of FIG. 15c illustrating the disposition of a tissue-engaging barb in accordance with the principles of the invention.

FIG. 15e is an enlarged plan view of portion B of the wire frame of FIG. 15c illustrating the details of the wire configuration in the wire frame structure.

FIGS. 15g and 15f are rear elevational and rear side elevational views of the wire frame of the filter device of FIG. 15a.

FIGS. 16a and 16b respectively are a side elevational view and a plan view of another access system in accordance with the principles of the present invention.

FIGS. 17a, 17b and 17c respectively are a side elevational view, a plan view and a cross-sectional view of another delivery system tube in accordance with the principles of the present invention.

FIGS. 18a and 18b are respectively are a side elevational view and a plan view of the delivery system tube of FIG. 17a and the access system sheath of FIG. 16a in a locked position in accordance with the principles of the present invention.

DETAILED DESCRIPTION OF THE INVENTION

Devices for filtering or otherwise modifying blood flow between a left atrial appendage (LAA) and its associated atrium may be implanted in the LAA. A catheter access sheath is percutaneously coursed through a blood vessel leading to the heart to gain access to the LAA. A delivery system is used to move the device through the access sheath into the LAA. The delivery system includes a shaft or wire to control movement of the implant device.

Atrial fibrillation results in harmful clot formation primarily in the LAA. Therefore, it is anticipated that the invention will be mostly used for filtering blood flow from the LAA. However, it will be understood that the invention may also be used for the right atrial appendage and in general for device placement across any aperture in the body through which blood flows.

The implant filter devices may have adjustable sizes. A compact or narrow size is used for percutaneous device delivery to the atrial appendages, for example, by cardiac catheterization. The devices include size-adjusting expansion mechanisms that allow the device size to be enlarged in situ to an expanded size. Alternatively, the devices may have self-expanding elastic structures. The devices may be held in position in the atrial appendage by outward contact pressure exerted by the outer structures of the enlarged device against the atrial appendage walls. This outward pressure provides an interference-like fit of the device. The outward contact pressure may be a result of designed springiness or elasticity of the device structure itself. Alternate or additional mechanical means such as inflatable balloons enclosed within the filter device also may be used to generate the outward pressure.

In addition (or as an alternate) to the pressure generated interference-like fit, tissue-engaging anchors may be used to hold an implanted device in place. These anchors are generally disposed on exterior device surfaces and engage atrial appendage wall tissue when the device is deployed in an atrial appendage. The anchors may be pins, hooks, barbs, wires with a traumatic bulb tips or any other suitable structures for engaging appendage wall tissue.

A variety of filter devices have been disclosed in U.S. patent application Ser. No. 09/428,008, U.S. patent application Ser. No. 09/614,091, U.S. patent application Ser. No. 09/642,291, U.S. patent application Ser. No. 09/697,628, and U.S. patent application Ser. No. 09/932,512, U.S. patent application Ser. No. 10/094,730, and U.S. patent application Ser. No. 10/200,565, all incorporated by reference herein. Other filter devices are disclosed herein, for example, expandable devices 700 and 100. These devices are described herein with reference to FIGS. 13a-13e, FIGS. 14a and b, and FIGS. 15a-15g.

Figure 13A:
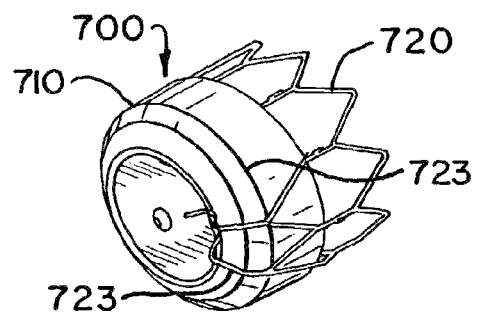
FIG. 13a is a rear side elevational view of an expanded filter device showing a filter membrane and portions of the expandable wire frame on which the filter membrane is supported in accordance with the principles of the invention.

FIGS. 13a-13e show expandable filter device 700 having a filter membrane cover 710. In FIG. 13a filter device 700 is shown in its natural or expanded state. Filter membrane 710 is supported on an elastic wire frame 720, which has the general shape of a cylinder that is closed at one end. Filter membrane 710 covers the closed cylinder end and extends along the sides of the cylindrical wire frame 720. Filter device 700 includes an insert or pin 715 having a socket 716 that is suitably adapted for attaching filter device 700 to a device tether or shaft (e.g., tether wire 410, FIG. 3c).

Device 700 may be expelled from the delivery tube at a suitable deployment location in the atrial appendage where it (device 700) can expand to its deployment state or natural size. When device 700 is deployed in an atrial appendage, filter membrane 710 stretches across or covers the atrial ostium and intercepts blood flowing in and out of the atrial appendage. Filter membrane 710 is made of blood-permeable material having fluid conductive holes or channels extending across membrane 710. Filter membrane 710 may be fabricated from any suitable biocompatible materials. These materials include, for example, ePFTE (e.g., Gortex®), polyester (e.g., Dacron®), PTFE (e.g., Teflon®), silicone, urethane, metal fibers, and other biocompatible polymers.

The hole sizes in the blood-permeable material may be chosen to be sufficiently small so that harmful-size emboli are filtered out from the blood flow between the appendage and the atrium. Suitable hole sizes may range, for example, from about 50 to about 400 microns in diameter. In one embodiment, filter membrane 710 is made of a polyester (e.g., Dacron®) weave or knit having a nominal hole size of about 125 um. The open area of filter membrane 710 (i.e., the hole density) may be selected or tailored to provide adequate flow conductivity for emboli-free blood to pass through the atrial appendage ostium. Further, portions of filter membrane 710 may be coated or covered with an anticoagulant, such as heparin or another compound, or otherwise treated so that the treated portions acquire anti-thrombogenic properties to inhibit the formation of hole-clogging blood clots.

Figure 13C:
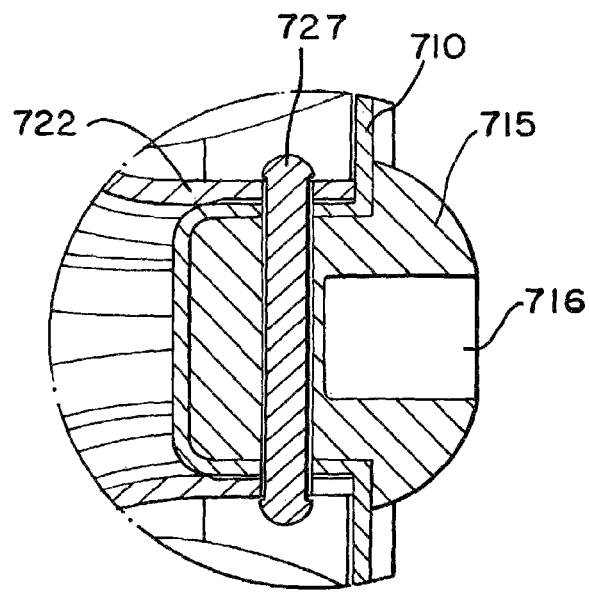
FIG. 13c is an enlarged cross sectional view of the central portion B of the filter device of FIG. 13b illustrating the attachment of the filter membrane to the wire frame structure in accordance with the principles of the invention.
Figure 13D:
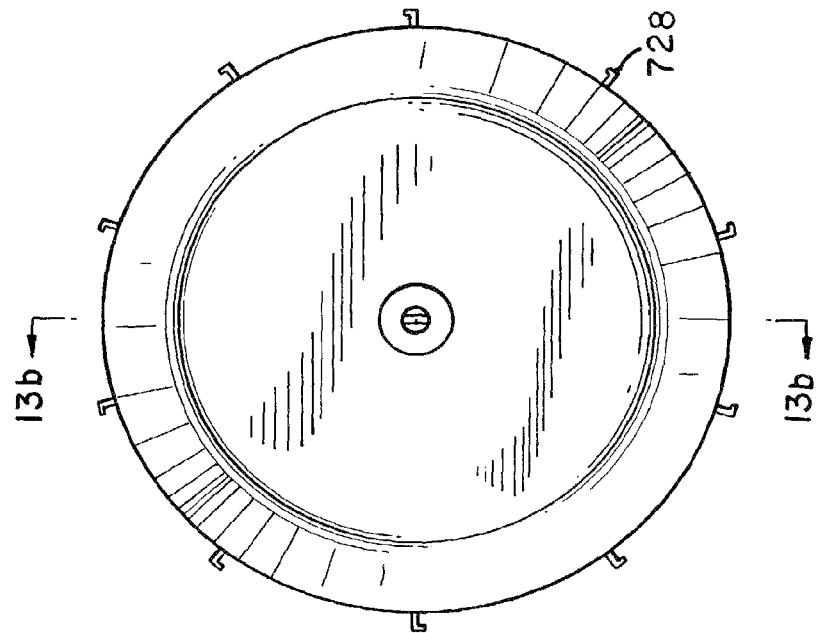
FIG. 13d is a cross sectional view of the expanded wire frame structure of FIG. 13b sectioned at plane A-A, illustrating barb elements suitable for engaging atrial appendage wall tissue to secure the position of the deployed device in an atrial appendage in accordance with the principles of the invention.
Figure 13B:
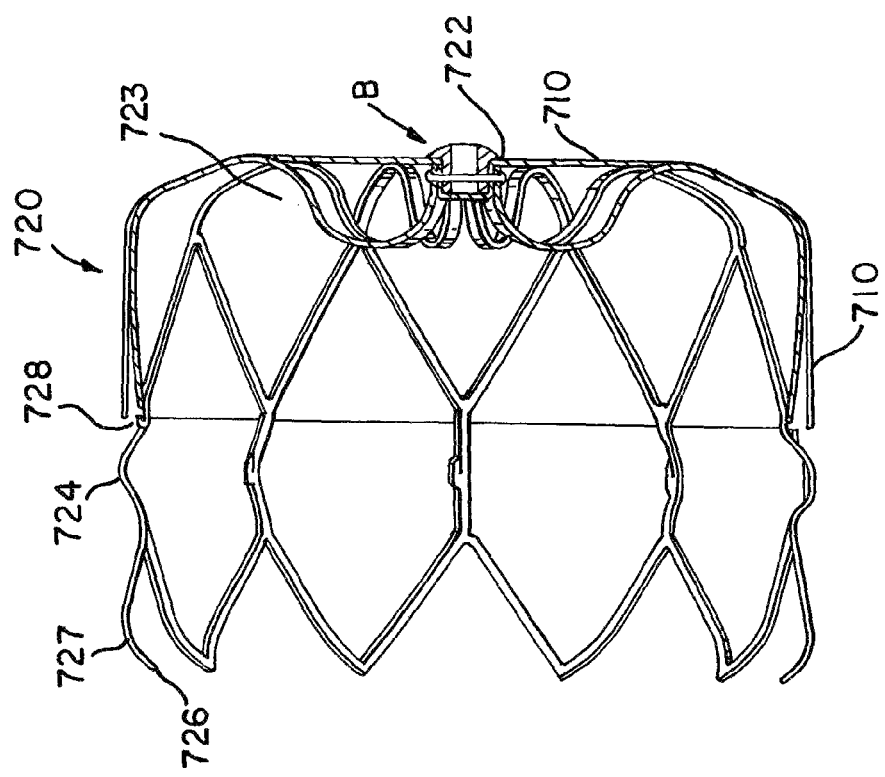

FIG. 13b illustrates the structure of wire frame 720. Wire frame 720 has a generally cylindrical structure that is closed at one end (right end). Wire frame 720 may be designed to have a lightweight open structure. For example, wire frame 720 may have an open structure that resembles that of a chicken wire mesh. The wire sizes in wire frame 720 may be suitably chosen with consideration to the structural strength and elastic properties of the fabrication material used (e.g., nitinol). In practice, the nitinol wires that are used in wire frame 720 may have typical cross-sectional dimensions, which range from a few mils to several tens of mils (one mil.=one thousandth of an inch).

At the proximal end (right end) of wire frame 720, the frame wires terminate in a cylindrical collar 722. Collar 722 is preferably located within the back plane of wire frame 720 (i.e., to the left of the plane of filter membrane 710, FIG. 13b). The cylindrical side portions of wire frame 720 are suitably shaped to engage atrial appendage wall tissue and provide, for example, an interference fit in the atrial appendage in which filter device 700 is deployed. Other portions of wire frame 720 may be shaped to serve as resilient springs, which push or bias the cylindrical side portions of wire frame 720 radially outward. FIG. 13b shows, for example, S-shaped wire portions 723, serve as resilient springs to expand wire frame 720 to its natural or unconstrained size. S-shaped wire portions 723 emanate from wire collar 722, and lie in the radial planes passing through passing through the cylindrical axis of wire frame 720. The S-shape of wire portions 723 causes collar 722 (and insert 716) to be geometrically recessed relative to the back plane of wire frame 720.

In addition, to geometrical shape features designed to retain or hold device 700 in position inside an atrial appendage, wire frame 720 may have barbs 728 along its outer surface to engage atrial appendage wall tissue. Barbs 728 may be distributed in any suitable pattern on the outer surface. FIGS. 13b, 13c and 13d show, for example, barbs 728 which are equally spaced along a circumference of wire frame 720. Further, the diameter of cylindrical wire frame 720 may be varied by design to enhance device retention in an atrial appendage. For example, wire frame 720 may have an outwardly distending ridge 724 that is designed to mechanically bias barbs 728 outward in an orientation suitable for engaging appendage wall tissue.

The diameter of cylindrical wire frame 720 also may be varied by design along its longitudinal axis to obtain device shapes or structures that reduce the likelihood of traumatic or undesirable tissue contact in device use. For example, the distal wire ends (at left open end 726) of frame 720 may be turned radially inwards toward the longitudinal frame axis. With the wire ends turned inward only smooth or rounded wire portions 727 of frame 720 may come in contact appendage walls. Thus, there is less likelihood of sharp or pointed wire ends coming in contact with or puncturing atrial appendage walls or other tissue. Alternatively or additionally, the frame wires may terminate in atraumatic tips at left open end 726 of wire frame 720.

Figure 13E:
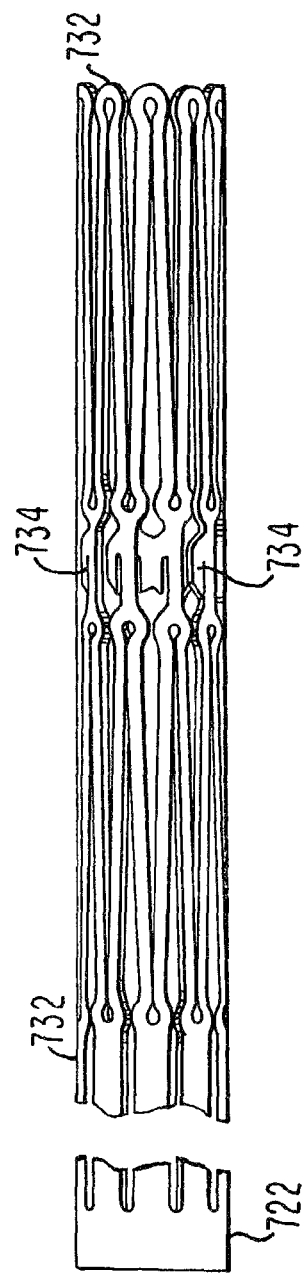
FIG. 13e is a side elevational view of a solid preform used in fabricating the expanded wire frame structure of FIG. 13b in accordance with the principles of the invention.

Filter device 700 may be fabricated with different-sized wire frames 720 as necessary or appropriate for use in different sizes of atrial appendages. An exemplary wire frame at its natural expanded size may be about an inch in diameter and about an inch long. As mentioned earlier, wire frame 720 may be made of suitable elastic material such as nitinol. Wire frame 720 may be made, for example, by machining a solid preform from a nitinol tube by laser cutting or other suitable machining processes. Other fabrication methods such as braiding nitinol wires may be alternatively used. FIG. 13e shows, for example, preform 730 fabricated by laser cutting a nitinol tube. Wires 732 of preform 730 terminate in cylindrical collar 722. Wires 732 may have attached stubs 734 which when turned upwards form tissue-engaging barbs 728. Preform 730 may be heat treated and shaped over a mandrel (not shown) to fabricate wire frame 720 having a desired geometrical shape, for example, as shown in FIG. 13b. In a compressed state, wire frame 720 returns to a narrow diameter tubular shape (not shown) similar to that of preform 730 that is convenient for fitting device 700 in a narrow diameter catheter or delivery tube for percutaneous delivery.

FIG. 13c is an enlarged cross sectional view of the central portion B of filter device 700 illustrating details of the co-assembly of filter membrane 710, insert 715, and wire frame 720 in device 700. Portions of filter membrane 710 are held firmly between the inner surfaces of cylindrical collar 722 and the outer cylindrical surfaces of insert 715, which is inserted in cylindrical collar 722. (Other portions of filter membrane 710 may be tied (e.g., by suitable sutures or wire strands) or glued at one or more places to wire frame 720 to hold filter membrane 710 against wire frame 720). Insert 715 has a threaded socket 716 (threads not shown) to which a mating screw or threaded tether wire can be attached. Insert 715 may be made of any suitable rigid materials that can be molded or machined to form threaded socket 716. Insert 715 may, for example, be made from hard plastics or metals such stainless steel or titanium. Insert 715 may have a diameter designed to provide a suitable interference fit in collar 722 to hold the filter device assembly together. Additionally or alternatively, mechanical means, for example, cotter pin 717, may be used to hold insert 715 in place. Alternative mechanical methods such as riveting or the use of adhesives or epoxies also may be used to hold insert 715 in place.

Figure 14A:
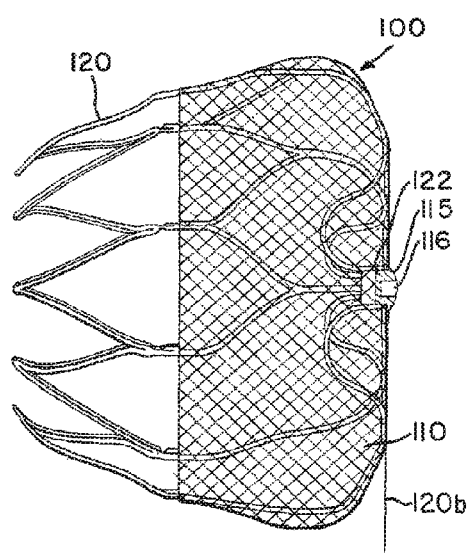
FIG. 14a is a side elevational view of another expanded filter device showing a filter membrane and portions of an expandable wire frame on which the filter membrane is supported in accordance with the principles of the invention.

Device 700 as shown in FIGS. 13*a* and 13*b* has substantially the same cylindrical diameter over substantial portions of its cylindrical length. In other embodiments of the device, the cylindrical diameter may vary by design. FIG. 14*a* shows an expandable filter device 100 whose cylindrical diameter decreases substantially over its (100) longitudinal axis.

FIG. 14*a* shows filter device 100 in its expanded state. Filter device 100 has a generally cone-like cylindrical shape that is closed at one end. Filter device 100 includes a filter membrane 110 covering portions of a wire frame 120 and includes other structures or features, which are the same or similar to the corresponding structures in filter 700 described above. For brevity, the description of device 100 herein is generally limited only to its features that may differ significantly from the corresponding structures or features of device 700.

In its expanded state wire frame 120 has a generally cone-like cylindrical structure, which is closed at one end (right end). FIGS. 15*a*-15*f*, illustrate the structure of exemplary wire frame 120, which may be made from a laser-cut solid nitinol tube preform. The varying cylindrical diameter of wire frame 120 is chosen to give device 100 a conical shape in consideration of the typical shapes of atrial appendages in which the device is likely to be used.

At the right end of wire frame 120, wires 120*w* that form wire frame 120 terminate in cylindrical collar 122. FIG. 15*b* shows an enlarged view of collar 122 and portions of attached wires 120*w*. Wires 120*w* are shown, for example, as approaching and terminating at collar 122 at a suitable shallow angle relative to the longitudinal axis of wire frame 120.

Figure 14B:
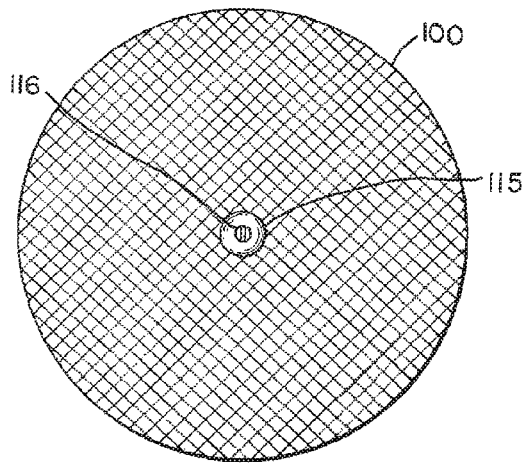

Filter device 100 includes a cylindrical insert 115 having a socket 116 that is suitably configured for attaching filter device 100 to a device tether or shaft (similar to insert 715 in device 700, FIG. 13*c*). Insert 115 is attached to collar 122 of wire frame 120 (FIG. 14*a*). Collar 122 may have holes 129 suitable for receiving, for example, cotter pins to fasten insert 115 in position. FIG. 14*b* shows, for example, the relative radial sizes of wire frame 120, insert 115 and socket 116.

The positioning of collar 122 along the longitudinal axis of wire frame 120 may be suitably chosen with consideration to the exterior surface topography presented by deployed device 120 to atrial blood flow. The recessed location of collar 122 may reduce or minimize the extension or protrusion of insert 115 normal to the back plane of device 100. Atrial appendage implant devices with few or little back plane protuberances may be desirable as such devices are unlikely to impede or disrupt blood flow through the atrium.

In preferred embodiments of either device 700 or 100, their respective wire frame structures 720 or 120 are shaped so that annular portions of their proximal surfaces (closed end) are concave or dimpled toward the distal end of the device (see, e.g., FIG. 13*b* and FIG. 14*a*). This concavity allows wire frame collar 722 (122) to be positioned along the longitudinal axis of wire frame 720 (120) at or about the closed-end back plane (e.g., back plane 120*b*, FIGS. 14*a* and 15*a*). With the wire collars so disposed, filter membrane 710 (110), which is held between the collar 722 (122) and insert 715 (115), may be supported over the closed end of wire frame 722 (122) in a substantially flat configuration (see e.g., FIG. 13*a* and FIG. 14*a*). Further, inserts 715 and 115 may have suitably small axial dimensions so that they do not protrude from or do not extend substantially beyond the devices' closed-end back planes (120*b*). Devices 700 or 100 of these preferred embodiments, when deployed in an atrial appendage, present a relatively flat proximal surface topography that does not protrude into the atrium or significantly disturb atrial blood flow past the appendage opening.

The concavity of portions of the back surface of the wire frames also may give portions of the wire frames an S-shape. These portions (e.g., sections 723, FIG. 13*a*, sections 123, FIGS. 14*a* and 15*a*) may serve as S-shaped resilient springs that push the cylindrical side portions of the wire frames radially outward to engage atrial appendage walls. Wire portions 123*c*, for example, with reference to FIG. 15*c*, form the chicken-wire mesh-like cylindrical sides portions of wire frame 120. At one end each S-shaped wire section 123 is attached to collar 122. The other end of each S-shaped wire section 123 is connected to wire portions 123*c*. FIG. 15*e* shows an enlarged view of an exemplary mechanical transition from a S-shaped wire section 123 to distal chicken-wire mesh-like wire portions 123*c*. S-shaped sections 123 may lie in radial planes that intersect each other along the longitudinal frame axis (FIG. 15*g*)

Filter devices 100 or 700 (or other expandable devices) may be implanted in a patient's atrial appendage using percutaneous catheterization procedures. The catheterization procedures involve first deploying an access system to position an access sheath through a patient's vascular system to the interior locations in the patient's heart, (e.g., to the atrial appendage). The access sheath provides a passageway through which medical instrumentation such as probes or implant devices are passed from outside the patient's body to interior locations in the heart. Independent delivery systems may be used to deliver the probes or devices through the access sheath. The inventive delivery systems that may be used can be of one or more types (e.g., delivery system 200, 800 or 800A).

Figure 8:
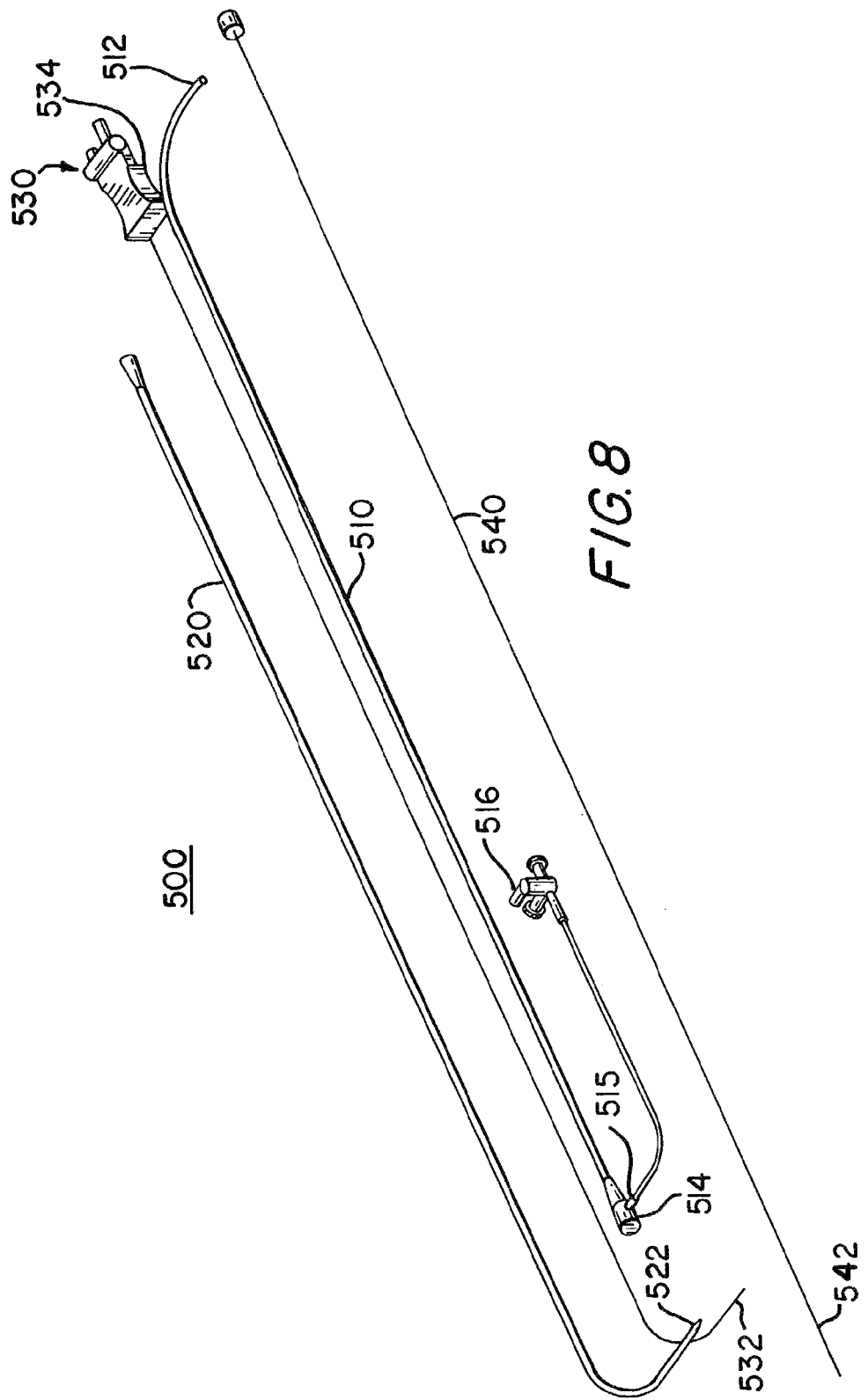
FIG. 8 is a side view of the components of a transseptal access system including a sheath, a dilator, a Brochenbrough needle and an obturator in accordance with the principles of the invention.
Figure 9:
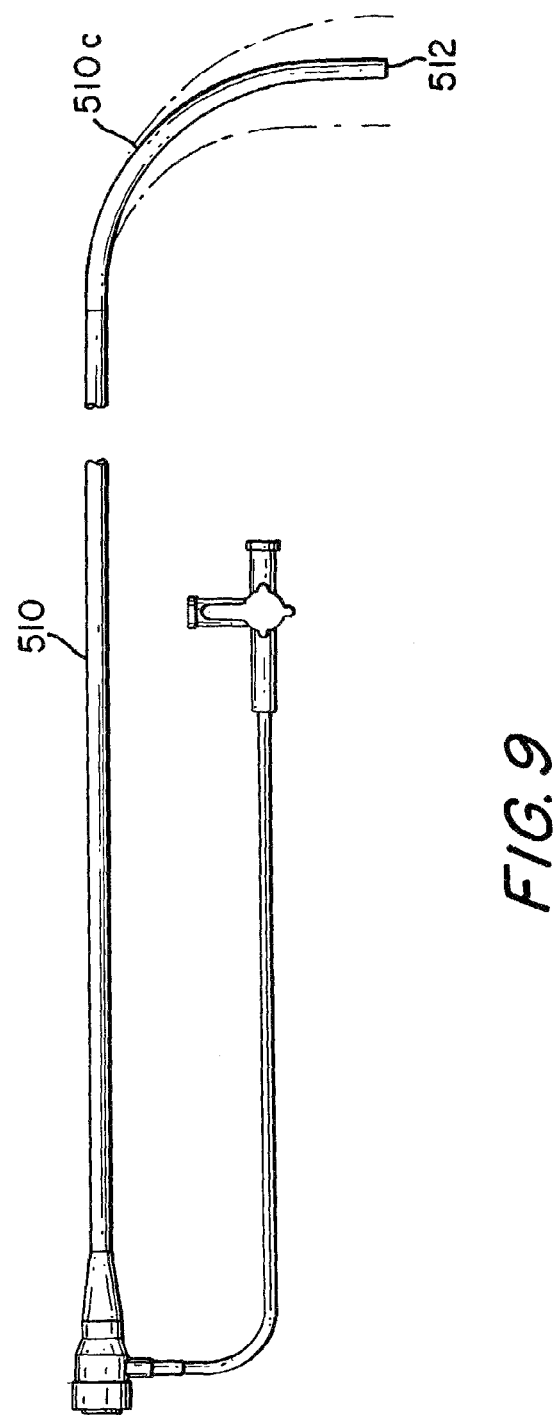
FIG. 9 is a plan view of an access system sheath in which the sheath tip has a simple curvature in accordance with the principles of the invention.

FIGS. 8 and 9 show access system kit 500 which may be used to establish a passageway for device delivery to an atrial appendage through a patient's vasculature. Access system kit 500 includes access sheath 510, dilator 520, obturator 540, and Brochenbrough needle 530. Access sheath 510 has a tubular structure. Access sheath 510 tubing may be made of any suitable flexible materials. Access sheath 510 may, for example, be made from braided wire tubing having a plastic outer coat. In the example, the braided wire may be stainless steel and the plastic outer coat may be any suitable plastic polymeric material such as urethane. The distal end or tip of the access sheath is made of curved tubing which can be stiffened or straightened as necessary during the insertion of the access sheath through the vasculature and across the cardiac septum. The curved shape of the access sheath tip may be designed to take into account the anatomical geometry of the vasculature and the heart.

The diameter of the tubing used to fabricate access sheath 510 is selected to be sufficiently large to allow convenient passage of probes or tubular portions of the implant device delivery systems (e.g., FIG. 2 delivery catheter tube 200) through it. An exemplary access sheath 510 is made from French size 12 (4 mm diameter) tubing. Other French size tubing (smaller or larger than French size 12) may be used as needed for different sizes of probes or implant devices. Further, the interior walls of the tubing material may be lined with lubricious material such as PTFE (e.g., Teflon®) for easier sliding passage of probes or implant device delivery systems through access sheath 510. The liner material may extend through the distal end of the tubing material to form a soft distal tip 512. The proximal end of the stainless tube is connected to valve assembly with fluid seals acting against tubes or catheters that may be inserted into the access sheath to prevent the leakage of fluids during use. For example, a hemostasis valve assembly 514 is attached to the proximal end of the sheath tube. Valve 514 may, for example, have a conventional hard plastic material shell construction with silicone material valve seals. Optional port 515 on the proximal end of access sheath 510 provides fluid communication with access sheath 510 lumen. A stopcock valve, for example, a three-way valve 516, may be used to control the flow of fluids through port 515.

Access system kit 500 components Brochenbrough needle 530, dilator 520, and obturator 540 may be conventional components suitably adapted to fit in access sheath 510 for use in conjunction with access sheath 510. Brochenbrough needle 530 is a hollow curved tube. Needle 530 may be made of any suitable material such as a stainless steel tube. Valve 532 seals the proximal end of the tube. The distal end of the tube is sharpened to form a needle tip 532. Obturator 540 is made from a length of a suitable solid wire having a blunt end 542. An exemplary obturator 540 is made from 14 mils diameter stainless steel wire. Obturator 540 is designed to slide through needle 520 with blunt end 542 extending out of needle tip 532. In use, the extension of blunt end 542 through needle tip 532 prevents needle tip 532 from causing inadvertent punctures of surrounding tissue or tubing. Dilator 520 is another curved hollow tube like-structure that can fit in access sheath 510. Dilator 520 also, may, for example, be made with from stainless steel tubing. Dilator 520 is designed to fit through access sheath 510 over needle 530.

Access system kit 500 may be used in a transseptal catheterization procedure for implanting filter devices, for example, in a patient's LAA. In such a catheterization procedure, access sheath 510, dilator 520, and needle 530 may be conventionally prepared for introduction into a patient's vascular system, for example, by flushing them with saline solution to remove air from their lumen. A conventional short introducer sheath or needle may be used to make a puncture opening, for example, in the right femoral vein (or artery), through which Brochenbrough needle 530 is introduced into the patient's vasculature. Alternatively, a puncture opening made by the sharpened needle tip 532 it self may be used to introduce needle 530 into the patient's vasculature.

Next, a length of conventional guide wire may be advanced through needle 530 (or the introducer sheath) ahead of the needle tip into the femoral vein. The guide wire may, for example, be a standard 35 mils diameter steel wire. Access sheath 510 and dilator 520 are then advanced over the guide wire through the femoral vein into the right superior vena cava. Dilator tip 522 may extend out of access sheath 510, for example, by about three quarters of an inch. Access sheath 510 and dilator 520 are advanced sufficiently into the right atrium through the right superior vena cava so that the dilator tip 522 is in close proximity to the atrial septum separating the right atrium from the left atrium. Next, the guide wire may be withdrawn and replaced by needle 530. Needle 530 (with obturator 540 extending through it) is advanced through dilator 520 so that needle tip 532 extends slightly out of dilator tip 522. Obturator 540 is then withdrawn to expose sharpened needle tip 532.

Next, needle 530, dilator 520, and access sheath 510 may be advanced, either sequentially or together, to puncture the septum, dilate the puncture opening, and advance access sheath 510 through the dilated septal opening into the left atrium. Once access sheath is set up across the septum, needle 530 and dilator 520 may be withdrawn.

Figure 1:
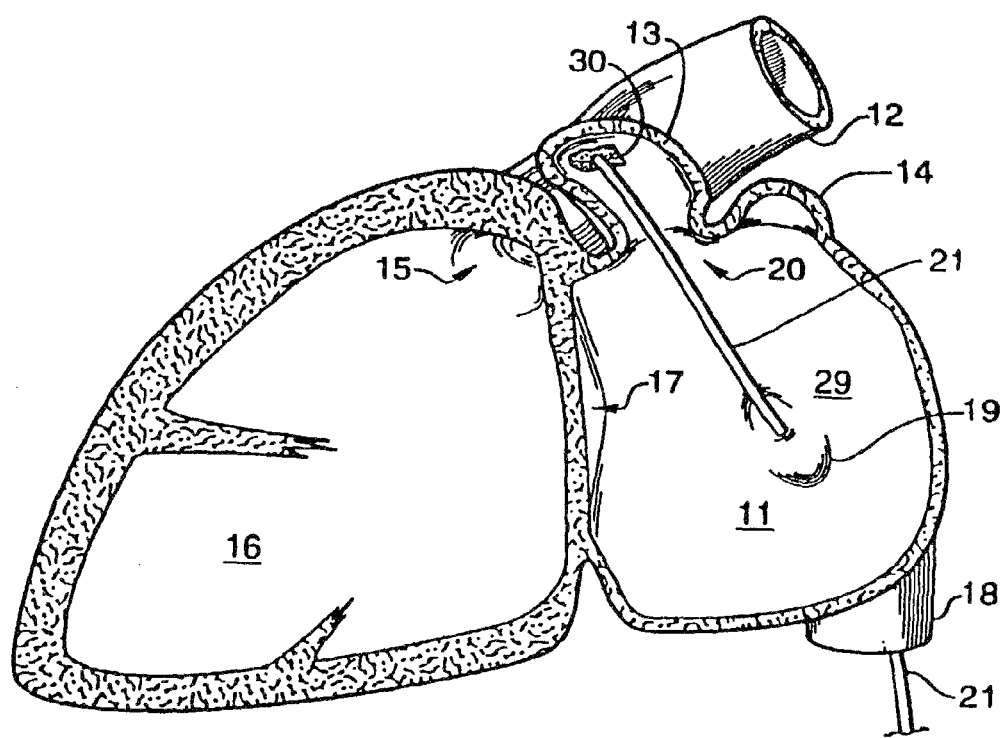
FIG. 1 is a partial cross sectional view of a heart illustrating the position of the left atrial appendage relative to the chambers of the heart and some of the major blood vessels.

A suitable septal puncture location may often be found within the thin walled dimpled region of the atrial septum (fossa ovalis), which is below the position of the LAA on the left atrium (FIG. 1). After advancing access sheath 510 through the dilated septal opening into the left atrium, access sheath 510 tip is reoriented and redirected from the direction of its entry into the left atrium toward the subject LAA. The curved shape of the distal access sheath 510 tip is advantageous in reorienting and redirecting it toward the subject atrial appendage. The curved shape may facilitate moving the access sheath through angles and in placing the access sheath in an orientation from which an implant device may be delivered directly into the subject atrial appendage. The sheath tip curvatures may be suitably designed to ease access to atrial appendages, which are anatomically disposed in the remote or awkward upper reaches of the corresponding atria. The suitable designed geometrical curvatures of the sheath tip may be simple or compound.

In one embodiment, access sheath 510 tip has a simple geometric curvature (e.g., J-shape). The length of the access sheath tubing may be chosen to have the ability to position distal end 512 in the atrial appendage. An exemplary access sheath 510 of this embodiment may have a length of about 33 inches (FIG. 9). The distal tip portion 510c of this exemplary sheath is a curved arc, which may have a radius of about a few inches (e.g., 2 inches). Distal tip portion 510c may be about one quarter of circle long. In another embodiment, access sheath 510 tip may have a geometrically compound curved shape. FIGS. 10, 11a and 11b show an exemplary access sheath 510 in which the sheath tip has two adjoining tip portions 510a and 510b. Portion 510a may have a radius of curvature of about a few inches, and may like portion 510c (FIG. 10) be about one quarter of circle long. Adjoining portion 510b may be a short stub-like portion, which extends from portion 510a and orients sheath exit opening (distal end 512) in a direction that is about normal or away from the plane containing curved portion 510a (FIGS. 11a and 11b).

With reference to and in continuation of the preceding description of a transseptal access procedure using access system kit 500, it will be understood that suitably curved access sheath 510 may be set up across the septum so that its distal end 512 points toward the subject LAA. Access sheath 510 may be further advanced into the LAA itself. In some procedures, access sheath 510 may be advanced so that distal end 512 is placed deep inside the LAA. Once access sheath 510 is placed in suitable position across the septum, it may be used as a passageway for delivery of filter devices to the LAA from outside the patient's body. Suitable delivery systems may be used to move the filter devices through hemostatic valve assembly 514.

During the transseptal access sheath positioning or set-up procedure described above, blood flow in needle 530 lumen may be sampled through valve 534, for example, to confirm the position of needle tip 532 in either the right or the left atrium. Additionally or alternatively, fluids may be injected into the heart through access sheath 510 using through port 515 for diagnostic or other purposes. For example, radio opaque dyes may be injected into the left atrial appendage to size the appendage to determine or select the appropriate or suitable implant device size. A selected device may be implanted in the LAA through the through the passage way formed by pre-positioned access sheath 510.

Inventive delivery systems may be used to implant the device through access sheath 510. FIG. 2 and FIGS. 3*a*-3*c*, show, for example, a delivery system 200 that may be used to deliver and position implant devices (e.g., filter device 700 and device 100) in a patient's LAA through access sheath 510. Delivery system 200 includes delivery catheter tube 220 that distally extends into a tubular implant sheath 230. The proximal end of delivery tube 220 is slidably connected to a hollow handle or manifold assembly 210. Delivery tube 220 may be partially retractable into manifold assembly 210. A tether wire 410 passes through hollow handle 210 and delivery tube 220 into implant sheath 230 (FIGS. 3*a*-3*c*). The distal portions of tether wire 410 may be encased in a flexible material, for example, distal flex coil 420 whose diameter is selected to fit inside implant sheath 230. The distal end of tether wire 410 terminates in fixture 430 suitable for attaching an implant device (FIG. 3*a*). Fixture 430 may, for example, be a threaded screw, which can be screwed into threaded socket 716 to attach, for example, filter device 700 (FIG. 13*a*). The proximal end of tether wire 410 is attached to a rotatable knob 260 mounted on handle 210. Rotatable knob 260 may be manually rotated to turn fixture 430.

The implant device selected for implantation in the patient is attached to distal tether wire fixture 430, compressed or compacted to a narrow diameter size and loaded in implant sheath 230. Implant devices having threaded sockets (e.g., device 700 insert 715, FIG. 13*a*) may be attached (or detached) to tether wire 410 by turning rotatable knob 260. Handle or manifold assembly 210 may be fitted with a mechanical safety cap 280 to cover rotatable knob 260 to prevent inadvertent unthreading or detachment of an attached device. To gain access to knob 260, an operator must first remove safety cap 280. The attached device is compressed in size (e.g. compressed device 700*a*, FIG. 3*b*) to fit in implant sheath 230. The walls of implant sheath 230 restrain compressed device 700*a* from expanding during device delivery. For deployment in situ, compressed device 700*a* is expelled from implant sheath 230 from a suitable deployment position in or about the subject LAA.

Compressed device 700*a* may be unconstrained or expelled from the implant sheath 230 for deployment by retracting delivery tube 220 over tether wire 410 into handle 210. Delivery system 200 includes external control mechanisms, which may be activated to retract delivery tube 220 over tether wire 410. In an embodiment of delivery system 200, the proximal end of delivery tube 220 is attached to reciprocating sheath actuator 240. Sheath actuator 240 may slide along handle or manifold assembly 210 to partially retract delivery tube 220 into manifold 210 or to further extend delivery tube 220 from manifold 210. Additionally, manifold 210 may be fitted with an optional actuator lock 290 to prevent inadvertent movement of sheath actuator 240. Movement of sheath actuator 240, may be enabled only after actuator lock 290 must be removed.

Sheath actuator 240 may have suitable hemostatic fluid seals (e.g., rubber seals 242, FIG. 5) acting against the surface of tether wire 410 passing through handle 210. The fluid seals may prevent fluid leakage from delivery tube 220 as sheath actuator 240 is moved along handle 210 over a length of tether wire 410. Sheath actuator 240 also may include an optional pipe fitting, for example, female luer fitting 245, in fluid communication with delivery tube 220 lumen. Fitting 245 may, for example, be used to flush delivery tube 220 with saline solution prior to use to remove air from delivery tube 220 lumen. Fitting 245 also may be used to sample blood or for infusion of drugs and other fluids into delivery tube 220 during use.

In the device implantation procedure, delivery system 200 is inserted into pre-positioned access sheath 510 through hemostasis valve assembly 514. Delivery tube 220 is advanced through access sheath so that implant sheath 230 extends out of access sheath tip 512 toward the subject LAA.

The length of catheter delivery tube 220 (and that of tether wire 410) desired for a catheterization procedure may be chosen or determined by consideration of length of the vascular pathway to the atrial appendage. Catheter delivery tube 220 lengths of about 80 cms. to 125 cms. may be appropriate for most adult catheterization procedures. Implant sheath 230 may have a length sufficient to axially cover distal flex coil 420 and the compressed implant device. The diameter of delivery catheter tube 220 and implant sheath 230 are kept small in consideration of the size of typical vascular pathways and the flexibility required for delivery catheter tube 220 and implant sheath 230 to traverse access sheath 510.

In an exemplary delivery system 200, the inside diameter of delivery tube 220 may be about 45 mils. Implant sheath 230, which constrains unexpanded filter devices, may have a larger diameter of about 90 mils to accommodate the larger diameter of an unexpanded filter device. (It will be understood that in practice a wide range delivery tube 220 and implant sheath diameters may be used as appropriate). In the example, tether wire 410, which passes through delivery tube 220, has a diameter smaller than 45 mils so that it can easily slide through delivery tube 220. An embodiment of tether wire 410 is made from a nitinol or other metal wire having a diameter of about 35 mils over most of its length. A metal wire of this diameter may be sufficiently stiff or rigid to allow for its smooth passage through delivery tube 220, and for mechanically coupling the motion of knob 260 to that of a filter device attached to the other end of tether wire 410. However, a distal section 432 of tether wire 410 of this embodiment may have a reduced diameter of about 10 mils (FIG. 3*a*). The diameter decreases gradually from a proximal section 436 diameter (35 mils) to a distal section 432 diameter (10 mils) over a taper section 434. Taper section 434 may have a length, for example, of about 1 to 2 cms.

This manner of wire diameter reduction lessens the coupling stiffness between tether wire 410 and a filter device attached to fixture 430. The lessening of coupling stiffness may allow the filter device deployed in an atrial appendage to be detached or released from device tether 410, without significant recoil. Recoilless release or release with minimum recoil is desirable as recoil may cause the deployed device to tip or dislodge from its pre-release position in the atrial appendage. The reduced coupling stiffness also allows the attached filter device to deploy in its natural unbiased state in the atrial appendage while still attached to the tether wire. These features may be advantageously used to assess the suitability of an implant deployment prior to detachment of tether wire 410. The deployed device may be viewed in its unbiased state while it is still attached to tether wire 410. An improperly or unsuitably deployed device may be retrieved, for example, by extending implant sheath 230 over still-attached tether wire 410 to recapture the device or by pulling the device back into implant sheath 230 with still-attached tether wire 410.

FIG. 3*c* shows a distal section of tether wire 410 of the aforementioned embodiment. FIG. 3*c* also shows an expanded filter device (e.g., device 700) attached to the distal end of tether wire 410. Portion 410*b* represents the section of tether wire 410 with the wire diameter reduced to about 10 mils. Portion 410b is encased in distal flex coil 420. The latter may be made of coiled or molded plastic elastomer material. Flex coil 420 is designed to have a diameter to occupy the luminal space between the inner walls of implant sheath 230 and tether wire portion 410b. By taking up the dead space in implant sheath 230, distal flex coil 420 may prevent reduced diameter wire tether portion 410b from buckling when tether wire 410 is moved relative to implant sheath 230.

In some cases of the device implantation procedure using delivery system 200, access sheath 510 may be pre-positioned such that sheath tip 512 is itself advanced into the subject atrial appendage. In other cases, access sheath 510 may be pre-positioned such that sheath tip 512 is outside or at the atrial appendage opening. In either instance, implant sheath 230 may be advanced out of access sheath tip 512, for example, to the back of the subject LAA, in preparation for device deployment. Then access sheath 510 may be partially retracted to pull access sheath tip 512 clear of the subject atrial appendage (if necessary) for device deployment. Access sheath 510 may be pulled back a sufficient distance so that tip 512 is back at the opening of the atrial appendage or is completely out of the atrial appendage. Next, the compressed implant device contained in the implant sheath 230 may be deployed in the atrial appendage by retracting implant sheath 230 to uncover compressed implant device 700a. Implant sheath 230 may be retracted over tether wire by sliding sheath actuator 240 backward over manifold 210 to retract delivery tube 210 into manifold 210 (e.g., FIGS. 2 and 5).

As implant sheath 230 is retracted, the implant device (e.g., device 700) expands in situ to its natural size. As filter device 700 expands, filter membrane 710 extends across the atrial appendage ostium to intercept blood flow. In the expanded device, cylindrical side portions of wire frame 720 press radially outward in opposition to the interior walls of the atrial appendage. Additionally, wire frame 720 features such as barbs 728 engage atrial appendage wall tissue. The outward contact pressures, which may be resisted by atrial wall muscle tissue, and the engagement of appendage wall tissue by barbs 728, secure the expanded device in an implant position. After filter device 700 is suitably expanded in situ, it may be released or detached from tether wire 410. To release filter device 700, first, safety cap 280 is removed to gain access to release knob 260. Next, release knob 260 may be turned or rotated to unscrew fixture 430 from socket 715 to release filter device 700 from tether wire 410.

It will be understood that suitable external imaging techniques may be used during the catheterization procedure to monitor the in vivo position of the components of the access system and the device delivery system. These techniques may include but are not limited to techniques such as radiography or fluoroscopy, echocardiography including transesophageal echocardiography, and ultrasound. It will also be understood that the various components of the device delivery system and the access system may include materials having suitable properties (e.g., radio-opacity) that make it possible to monitor the in-vivo component positions using the appropriate external imaging techniques.

For some assessment or imaging techniques, port 514 on access sheath 510 may be used to inject fluids into the heart including, for example, radio opaque dyes, at any suitable times in the procedure including when delivery catheter tube 210 extends through access sheath 510. In delivery system 200, delivery tube 220 lumen may be used to transmit fluids. For such use, flex coil portions in which distal portions of tether wire 410 are encased may include flush ports to allow fluids to be injected into the heart or atrial appendage through delivery tube 220 lumen. FIGS. 4a-4b show a coil 620, which may be used to encase the distal narrow diameter portions of tether wire 410. Coil 620 may be made of soft polymeric materials (including, for example, thermoplastic electrometric resins that may be sold commercially under the trade name PEBAX®). The outer diameter of coil 620 (like that of coil 420) may be about the same as the inner diameter of implant sheath 230. Coil 620 includes axial lumen 622 that leads to flush ports 624 near the distal end of coil 620. An exemplary lumen diameter may be about 75 mils. Proximal end portions 628 of coil 620 may be designed for mechanical connection with delivery tube 220. For example, proximal end portions 628 may be tapered to provide interference fit in delivery tube 220 (FIGS. 4a and 4b, delivery tube 220 not shown). Tether wire 410, which may have a diameter of about 35 mils or less, passes through delivery tube 220 and through coil 620 so that device-attachment fixture 430 extends out of coil 620. A mechanical restraint, for example, a cylindrical plug or stop 626 that fits in axial lumen 622, may be used to hold coil 620 in position over tether wire 410. Cylindrical plug 626 may be glued to tether wire 410 with suitable adhesives or epoxy material 627 (FIG. 4b inset). Fluid connectivity around plug 626 between delivery tube 220 lumen and axial lumen 622 may be provided by grooves and holes 629 fashioned in proximal end portions 628 of coil 620. Fluids that are injected into delivery tube 220 lumen (e.g., through fitting 245, FIG. 2) may pass through holes 629 into lumen 622 and are discharged from flush ports 624. This fluid pathway may, for example, be used to inject radio opaque dyes into atrial appendages around implant devices that are still attached tether wire 410. Such radio opaque dye injection may be advantageous in assessing the positioning of expelled or deployed devices in the atrial appendage before tether wire 410 is detached. If the position of the expelled device is not appropriate, sheath actuator 240 may be activated to slide implant sheath 230 forward over tether wire 410 to recapture the device for repositioning or withdrawal as desired.

In other embodiments of the device delivery system, tether wire 410 itself may be used as the primary means to control movement of the attached implant device in and out of implant sheath 230. FIGS. 6 and 7 show, for example, delivery system 800 in which the movement of tether wire 410 through delivery catheter tube 220 controls the movement of the attached implant device in or out of implant sheath 230 (implant device not shown). For brevity, the description of delivery system 800 herein is generally limited only to some of its features that may differ significantly from the corresponding structures or features of delivery system 200.

Device delivery system 800 includes delivery catheter tube 220 that distally extends into a tubular implant sheath 230. The to be implanted device is attached to tether wire 410 and is contained in implant sheath 230. A radial compression valve assembly 810 is mounted or connected to the proximal end of delivery catheter tube 220. Radial compression valve assembly 810 may, for example, be a large bore Touhy Borst valve assembly. The side-arm or Y-arm 814 of the Touhy Borst valve assembly allows intermittent or continuous flushing and contrast injection, and also allows for continuous blood monitoring through delivery tube 220 lumen. A multi-way stopcock 816 may be attached to Y-arm 814 to regulate or control the flow of fluids through Y-arm 814.

Tether wire 410 slidably passes through valve assembly 810 and delivery tube 220 into implant sheath 230. Touhy Borst valve assembly 810 seals permit unimpeded translational or rotational movement of tether wire 410, whose proximal end is attached to a control handle or knob 820. In use knob 820 may be manipulated to translate or rotate tether wire 410 as necessary at appropriate steps in the device implantation procedure. For example, to insert or deploy an attached device in the subject atrial appendage, tether wire 410 may be translated forward through hemostatis valve assembly 810 to push the attached device out of implant sheath 230. A rotational motion of tether wire 410 may be used to unthread and detach the deployed device.

Proximal portions of tether wire 410 leading to control knob 820 optionally may be clad by stiffening material or tube 822. Stiffening tube 822 may provide mechanical rigidity for transmitting, for example, control knob 820 rotation or torque to the threaded fixture 430 over the length of tether wire 410.

It will be understood that the various components of device delivery system 800 (e.g., knob 820, valve assembly 810, delivery tube 220, stopcock 816, etc.) may be mutually attached or connected using suitable adhesives, glues, and epoxy materials, and/or conventional fittings. Some or all sections of deliver system 800 may be fabricated using off-the-shelf components or alternatively may be fabricated as single pieces using techniques such as injection molding. For example, pipefitting or locking nut 812 may be used to connect delivery tube 220 to threaded portions of valve assembly 810.

Delivery system 800 and access sheath 510 may optionally include fittings or other coupling mechanisms, which allow them to be mechanically coupled. The coupling mechanism may, for example, be a manually adjustable mechanical lock. The coupling mechanisms may, for example, include threaded nut connectors, bayonet connectors, pin connectors, screwed flanges, or any other suitable connectors which can be used to lock the access sheath and the delivery system together. The suitable connectors may include pipefittings such as leur fittings.

FIGS. 12a-12d show, for example, access sheath 510 and delivery system 800 with lock fittings or adapters 550a and 850a, respectively. Fitting 550a may, for example, be a socket or female adapter fashioned in hemostasis valve 514 at the distal hub of access sheath 510. Fitting 850a may be a pin or male adapter disposed over delivery tube 220 adjacent to valve assembly 810. Fittings 550a and 850a may have matching structures and dimensions that allow access sheath 510 and delivery system 800 to be mechanically coupled or joined together. Matching lock fittings 550a and 850a may be designed to be capable of ready and repeated physical engagement or disengagement (with or without the use of a tool). Access sheath 510 and delivery system 800 may be moved together when joined or combined by the coupling mechanism, or independently when the coupling mechanism is inactive. Mechanically coupling delivery system 800 to access sheath 510 may be advantageous in obtaining a stable passageway for moving implant devices attached to a tether wire. The mechanical coupling also may be useful in predetermining and fixing the relative positions of implant sheath 230 and access sheath tip 512, and in moving the two together.

FIGS. 12a and 12b show delivery system 800 and access sheath 510 in use, for example, during a catheterization procedure, with delivery catheter tube 220 inserted in access sheath 510 through hemostasis valve 514 with matched luer fittings 850a and 550a separated and disconnected. In this state both delivery catheter tube 220 and access sheath 510 can be moved independently. In routine operation, delivery catheter tube 220 may be advanced through access sheath 510 until fitting 850a locks in fitting 550a. When locked together, the distal end of implant sheath 230 may, for example, be flush with access sheath tip 512 (or at separation distance which is predetermined by the positioning of fitting 850a along the length of delivery tube 220).

FIGS. 12c and 12d show delivery system 800 and access sheath 510 with fittings 850a and 550a locked together. In the locked state both delivery catheter tube 200 and access sheath 510 move together in a mechanically joined or combined fashion. An implant device (e.g., device 100) may be deployed, for example, in the subject LAA, by retracting the delivery tube/access sheath combination over wire 410 to unsheathe the self-expanding implant device (FIG. 3, LAA not shown).

Other types of locks and/or valve assemblies may be incorporated in access system sheath 510 and delivery system tube 800. The configurations of these other types of locks and valves may provide different or additional operational features. For example, FIGS. 16a-18b show another access system sheath 510A and another delivery system 800A. Again for brevity, the description of delivery systems 800A and access system 510A herein is generally limited only to those features that may differ significantly from the corresponding structures or features of delivery systems 200 and 800 and access system 510.

Access system sheath 510A, shown in FIGS. 16a and 16b, may have a radial compression valve assembly 514A at its proximal hub. Radial compression valve assembly 514A may have any suitable conventional design. Valve 514A may, for example, have a Touhy Borst design with a cylindrical body 514c that houses a suitable radial shaft seal (not shown). The shaft seal may, for example, be made from a cylinder or ring of silicone material. A knurled knob 514k, which rotates on threaded portions of cylinder body 514c, may be used to controllably compress the shaft seal against a passing shaft or tube (e.g., delivery tube 220). The use of rotary valve 514A having an adjustable shaft seal may be advantageous in controlling back bleeding during the manipulation of the delivery tube or other instrumentation (e.g., guide wires) through access sheath 510A.

Access system sheath 510A may be used with a suitably adapted delivery system, for example, delivery system 800A shown in FIGS. 17a-17c. Delivery system 800A and access system sheath 510 may be locked together using suitable snap-on locking arrangements. The locking arrangement may restrict the relative translation and/or rotation of the two systems. A snap-on locking arrangement may include, for example, a C-shaped clip 852 that is disposed on the distal ends of delivery system valve assembly 810 (FIG. 17a). Further, cylinder body 514c of valve 514A at the distal end of access sheath 510 may be provided with suitable detents, grooves, holes or rings, to receive and hold the tips of C-shaped clip 852. For example, ring 552 on cylinder body 514C may be designed to receive and slidably hold the tips of C-shaped clip 852. Ring 552 may be immovably fixed on cylinder body 514c, or alternatively ring 552 may be rotatably mounted on cylinder body 514c. Like luer-type lock fittings 550a and 850a (FIGS. 12a-12b), C-shaped clip 852 may be designed to be capable of ready and repeated physical engagement or disengagement with ring 552.

In operation, delivery system 800A may be mechanically locked with access system 510A by suitably advancing delivery system 800A so that tips of C-shaped clip 852 catch or snap behind ring 552. The exemplary C-shape locking mechanism may mechanically couple delivery system 800A to access sheath 510A to obtain a stable passageway for moving implant devices attached to a tether wire, while allowing desirable rotational motion of delivery tube 220 and delivery system 800A. For example, C-shape clip 852 when locked prevents the linear or translation movement of delivery system 800A relative to access system sheath 510A. The rotational motion of delivery tube 220 passing through rotary valve 514A may remain unconstrained as the tips of C-shape clip 852 may slid around ring 552 (or alternatively ring 552 may rotate around cylindrical body 514c). Further, open spacing 852a that is delimited by C-shape clip 852 provides operator access to knob 514k. This access may be advantageously used to adjust knob 514k, for example, to control back bleeding during the device implantation or other procedures.

FIGS. 18a and 18b show delivery system 800A and access sheath 510A in use, for example, during a catheterization procedure, with delivery catheter tube 220 (not seen) inserted in access sheath 510A through rotary valve 514A with C-shape clip 852 locked on cylindrical body 514c. In the locked state both delivery system 800A and access sheath 510A may be moved together linearly. Delivery catheter tube 220 and delivery system 800A may be rotated as necessary or advantageous, for example, to orient or position the implant device (e.g., device 100) attached to the distal end of tether wire 410. Access to knurled knob 514k through spacing 852a allows the operator to adjust the radial or shaft seal of valve 514 around catheter tube 220 to allow free rotation and/or control back bleeding.

The design of systems 800A and 510 may incorporate other optional features involving operator use of the systems. For example, FIGS. 17a-18b show an additional locking clip 890 mounted on tether wire casing 822. Clip 890 may have a suitable releasable or detachable structure. Clip 890 may, for example, be a plastic flag or tab which is releasable, mounted in a slot running along casing 822 tube. Clip 290A acts as a stop against the distal end of Touhy Borst valve or manifold assembly 810. Clip 890 may be mounted at suitable distance along wire casing 822 to limit the length of tether wire 410 that can be inserted in delivery tube 220. By limiting the inserted length of tether wire 410, clip 890 may prevent premature expulsion and deployment of the implant device attached to the end of tether wire 410. In use, clip 890 may be removed or released by an operator after combination of access sheath 510A/delivery tube 800A has been suitably placed (e.g., in a subject LAA) for device deployment. Then the operator may extend additional lengths of tether wire 410 through delivery tube 220 to push the tethered device out of the constraining implant sheath 230 for device deployment. The deployed device may be released by turning control knob 820.

Delivery system 800A and tether wire 410 may include suitable features to prevent inadvertent release of the device attached to the distal end of tether wire 410. For example, proximal hub 832 of Touhy Borst assembly 810 (e.g., at the end opposite from clip 852) may include a D-shaped lumen or keyway for the passage of tether wire 410/casing 822. FIG. 19c shows, for example, D-shape keyway 815 that is located to the left of washer 819 and silicone seal 817. Portions or lengths of tether wire 410/casing 822 may have a suitable cross-section that allows it to slide through keyway 815 but which prevent its rotation. For example, casing length 822D may have a D-shaped cross-section that allows sliding passage of tether wire 410/casing 822 through keyway 815 but one that prevents rotation. Further, casing 822 at its extreme distal end portions abutting knob 820 may have a suitable cross-section that can rotate through the keyway 815. For example, short casing length 822R may have a round cross-section. In use, tether wire 410 is restrained from turning while casing length 822D is in keyway 815, which, may correspond to when the attached device is within implant sheath 230. Tether wire 410 can be turned only when knob 820 is pushed up against connector 812 so that round cross-section casing length 822R is within keyway 815. The length of tether wire 410 may be designed so when knob 820 is pushed up against connector 812 the implant device is pushed out of implant sheath 230. Thus the device may be detached by unscrewing tether wire 410 only after it has been has been expelled from implant sheath 230 by pushing knob 820 up against up against connector 812. The operator may, for example, release the deployed device by turning knob 820.

It will be understood that the foregoing is only illustrative of the principles of the invention, and that various modifications can be made by those skilled in the art without departing from the scope and spirit of the invention. It will be understood that terms like "distal" and "proximal", "left" and "right", and other directional or orientational terms are used herein only for convenience, and that no fixed or absolute orientations are intended by the use of these terms.

1. A blood filtration system for filtering blood flow from an atrial appendage, comprising: a filter device that is configured for deployment in the atrial appendage to intercept blood flow, wherein the filter device has an elastic structure that expands to its natural size from a compressed state when the device is unconstrained; a tubular access sheath for establishing a percutaneous pathway to the atrial appendage; and a delivery instrument for delivering the device through a lumen of the access sheath and for deploying the delivered device in the atrial appendage, wherein the delivery instrument includes: a delivery tube; and a movable tether that passes through the delivery tube, and that is releasably attached to the device, wherein the tether provides mechanical control over the delivery and deployment of the device, and wherein the access sheath and the delivery tube comprise releasable locks for controlling the relative movement of the two.

The invention claimed is:

1. A device configured for implantation in a left atrial appendage, the device comprising:
   a support structure having a proximal end, a distal end, and an intermediate portion extending between the proximal end and the distal end,
   wherein in an unconstrained condition diameters of the respective proximal end, distal end and intermediate portion of the support structure decrease distally over its longitudinal axis;
   a membrane extending along the intermediate portion and supported by the proximal end of the support structure,
   wherein the membrane is in a generally planar configuration along a plane at the proximal end of the support structure; and
   a plurality of tissue-engaging anchors disposed on the support structure distal of the membrane.

2. The device of claim 1, wherein the distal end of the support structure is an open end and the proximal end of the support structure is enclosed by the membrane.

3. The device of claim 1, wherein the plane is substantially perpendicular to a longitudinal axis of the device.

4. The device of claim 1, further comprising:
   a protrusion extending from adjacent the proximal end of the support structure,
   wherein the protrusion extends proximally from the plane.

5. The device of claim 4, wherein the protrusion comprise a threaded insert.

6. The device of claim 4, wherein the protrusion extends in a direction substantially perpendicular to the plane.

7. The device of claim 1, wherein the support structure comprises a proximal collar.

8. The device of claim 7, wherein the device includes a delivery configuration and a deployed configuration.

9. The device of claim 8, wherein the proximal collar is recessed and positioned distally of the plane when the device is in the deployed configuration.

10. The device of claim 1, wherein the support structure comprises:
 a plurality of struts defining a plurality of fenestrations and extending from the proximal end to the distal end of the support structure.

11. The device of claim 10, wherein the support structure comprises:
 a hub located near a radial center of the support structure; and
 wherein the plurality of struts extend from the hub.

12. The device of claim 10, wherein each strut of the plurality of struts forms an S-shape.

13. A system for implanting an implant in a left atrial appendage, the system comprising:
 a delivery catheter having an elongate flexible body with a proximal end and a distal end;
 a wire extending through the delivery catheter;
 an implant comprising:
 a support structure having a proximal end, a distal end, and an intermediate portion extending between the proximal end and the distal end,
 wherein in an unconstrained condition diameters of the support structure decrease distally over its longitudinal axis;
 a membrane extending along the intermediate portion and supported by the proximal end of the support structure; and
 a plurality of tissue-engaging anchors disposed on the support structure distal of the membrane,
 wherein the membrane is in a generally planar configuration along a plane at the proximal end of the support structure; and
 wherein a distal end of the wire is configured to be releasably attached to a proximal end of the implant.

14. The system of claim 13, wherein the distal end of the wire is configured to be releasable attached to a protrusion extending from adjacent a proximal end of the support structure, where the protrusion extends proximally from the plane.

15. The system of claim 14, wherein the protrusion extends in a direction substantially perpendicular to the plane.

16. The system of claim 13, wherein the distal end of the wire includes threads configured to engage threads on the proximal end of the implant.

17. The system of claim 13, wherein the plane is substantially perpendicular to a longitudinal axis of the support structure.

18. A blood filtration device for filtering blood flow from an atrial appendage, comprising:
 a proximal hub including a protrusion;
 a one-piece frame having a proximal end, a proximal portion, a distal portion, an intermediate portion between the proximal portion and the distal portion, and a distal end,
 wherein in an unconstrained condition diameters of the support structure decrease distally over its longitudinal axis;
 a blood-permeable membrane or mesh covering the proximal portion and at least a portion of the intermediate portion of the one-piece frame such that the blood-permeable membrane or mesh presents a generally planar surface; and
 a plurality of tissue-engaging anchors disposed on the support structure distal of the blood-permeable membrane,
 wherein the protrusion extends proximally from the generally planar surface.

19. The blood filtration device of claim 18, wherein the generally planar surface is substantially perpendicular to a longitudinal axis of the blood filtration device.

20. The blood filtration device of claim 18, wherein the protrusion extends in a direction substantially perpendicular to the generally planar surface.

* * * * *